United States Patent [19]
Chance

[11] Patent Number: 6,058,324
[45] Date of Patent: May 2, 2000

[54] EXAMINATION AND IMAGING OF BIOLOGICAL TISSUE

[75] Inventor: Britton Chance, Marathon, Fla.

[73] Assignee: Non-Invasive Technology, Inc., Philadelphia, Pa.

[21] Appl. No.: 09/170,833

[22] Filed: Oct. 13, 1998

Related U.S. Application Data

[63] Continuation-in-part of application No. PCT/US93/05868, Jun. 17, 1993, and a continuation of application No. 08/849, 202, Jun. 2, 1997, Pat. No. 5,820,558, which is a continuation of application No. PCT/US95/15694, Dec. 4, 1995, which is a continuation-in-part of application No. 08/349, 018, Dec. 2, 1994, Pat. No. 5,673,701.

[51] Int. Cl.$^7$ ........................................................ A61B 5/00
[52] U.S. Cl. ............................................ 600/473; 600/476
[58] Field of Search ................................ 600/310, 314, 600/317, 322, 473, 476; 356/35, 40, 41, 345

[56] References Cited

U.S. PATENT DOCUMENTS

| | | |
|---|---|---|
| 4,129,125 | 12/1978 | Lester et al. . |
| 4,223,680 | 9/1980 | Jöbsis . |
| 4,224,948 | 9/1980 | Cramer et al. . |
| 4,281,645 | 8/1981 | Jöbsis . |
| 4,321,930 | 3/1982 | Jöbsis et al. . |
| 4,515,165 | 5/1985 | Carroll . |
| 4,576,173 | 3/1986 | Parker et al. . |
| 4,700,708 | 10/1987 | New, Jr. et al. . |
| 4,714,341 | 12/1987 | Hamaguri et al. . |
| 4,773,422 | 9/1988 | Isaacson et al. . |
| 4,807,637 | 2/1989 | Bjorkholm . |
| 4,824,242 | 4/1989 | Frick et al. . |

(List continued on next page.)

FOREIGN PATENT DOCUMENTS

| | | |
|---|---|---|
| 0 099 756 | 1/1984 | European Pat. Off. . |
| 0 102 816 | 3/1984 | European Pat. Off. . |
| 2 068 537 | 8/1981 | United Kingdom . |
| WO 84/04665 | 12/1984 | WIPO . |
| WO 92/13598 | 8/1992 | WIPO . |
| WO 92/20273 | 11/1992 | WIPO . |
| WO 93/05686 | 12/1993 | WIPO . |

OTHER PUBLICATIONS

Arridge et al., "Reconstruction Methods for Infra–red Absorption Imaging", SPIE, vol. 1431:204, 1991.
Barlow et al., "Breast Biopsy Analysis By Spectroscopic Imaging", Photon Migration in Tissues, Plenum Press, New York, p. 111, 1989.

(List continued on next page.)

*Primary Examiner*—Eric F. Winakur
*Attorney, Agent, or Firm*—Fish & Richardson P.C.

[57] ABSTRACT

Optical methods and systems for in vivo, non-invasive examination of biological tissue include at least one light source constructed to emit light of a visible or infra-red wavelength for introduction into an examined tissue volume from at least one input port, and at least one detector constructed to detect light of the visible or infra-red wavelength that has migrated in the examined tissue volume from at least one input port to at least one detection port. The optical systems also include an optical array, a radiation controller, and a processor. The optical array includes the input and detection ports located in a selected geometrical pattern providing several average photon migration pathlengths in the examined tissue volume. Each arrangement of least one input port and at least one detection port provides one of the average pathlengths, wherein the average pathlength is characteristic of the tissue between one input port and one detection port. The radiation controller is constructed to sequentially control light emitted from the at least one input port and constructed to control detection of light of the introduced wavelength to define a null plane in the tissue volume for two of the arrangements of the input and detection ports. The processor is operatively connected to the radiation controller and is constructed to examine the biological tissue based on data corresponding to the introduced and detected light for at least two of the average pathlengths and the defined location of the null plane.

54 Claims, 25 Drawing Sheets

U.S. PATENT DOCUMENTS

| | | |
|---|---|---|
| 4,836,207 | 6/1989 | Bursell et al. . |
| 4,846,183 | 7/1989 | Martin . |
| 4,869,254 | 9/1989 | Stone et al. . |
| 4,908,762 | 3/1990 | Suzuki et al. . |
| 4,926,867 | 5/1990 | Kanda et al. . |
| 4,951,682 | 8/1990 | Petre . |
| 4,972,331 | 11/1990 | Chance . |
| 5,062,431 | 11/1991 | Potter . |
| 5,088,493 | 2/1992 | Giannini et al. . |
| 5,090,415 | 2/1992 | Yamashita et al. . |
| 5,122,974 | 6/1992 | Chance . |
| 5,158,090 | 10/1992 | Waldman et al. . |
| 5,174,298 | 12/1992 | Dolfi et al. . |
| 5,203,339 | 4/1993 | Knüttel et al. . |
| 5,213,105 | 5/1993 | Gratton et al. . |
| 5,257,202 | 10/1993 | Fedderson et al. . |
| 5,309,907 | 5/1994 | Fang et al. . |
| 5,309,912 | 5/1994 | Knüttel . |
| 5,353,799 | 10/1994 | Chance . |
| 5,416,582 | 5/1995 | Knutson et al. . |

OTHER PUBLICATIONS

Britton Chance, "The Future of Time Resolved Spectrocopy and Imaging" Mind Brain Imaging Program, Aug. 5–Aug. 5–10, 1990, Hamamatsu, Japan.

Cui et al., Experimental Study of Migration Depth for the Photons Measured At Sample Surface, SPIE 1431:180 1991.

Fishkin et al., "Diffusion of Intensity Modulated Near–Infrared Light in Turbid Media", SPIE 1431:122, 1991.

Gratton et al., "The Possibility of a Near Infrared Optical Imaging System Using Frequency Domain Methods", Mind Brain Imaging Program, Aug. 5–10, 1990, Hamamatsu, Japan.

Greenfeld, "A Tissue Model for Investigating Photon Migration in Trans–Cranial Infrared Imaging", Photon Migration Tissues, Plenum Press (New York), p. 147, 1989.

Grunbaum et al., "Diffuse Tomography", SPIE 1431:232, 1991.

Haida et al., "A Method to Estimate the Ratio of Absorprtion Coefficients of Two Wavelengths Using Phase–Modulated Near Infrared Light Spectroscopy", Analytical Biochemistry, vol. 208, pp. 348–351, 1993.

Oda et al., "Non–Invasive Hemoglobin Oxygenation Monitor and Computerized Tomography of NIR Spectrometry", SPIE 1431:284, 1991.

Sevick et al., "Analysis of Absorption, Scattering and Hemoglobin Saturation Using Phase Modulation Spectroscopy", SPIE 1431:264, 1991.

Sevick et al., "Photon Migration in a Model of the Head Measured Using Time–and–Frequency–Domain Techniques Potentials of Spectroscopy and Imaging", SPIE 1431:84, 1991.

Sevick et al., "Quantitation of Time–and Frequency–Resolved Optical Spectra for the Determination of Tissue Oxygenation," Analytical Biochemistry, 195:330–351, 1991.

Singer et al., "Image Reconstruction of the Interior of Bodies that Diffuse Radiation", Science 248:990, 1990.

Yamashita et al., "The Neonate Brain (NIR) and Breast Imaging Using Transillumination", Photon Migration in Tissues, Plenum Press, New York, p. 55, 1989.

Brochure, Becton Dickinson, Cardio–Green® (CG®) HW&D Brand of Sterile Indocyanine Green, USP, Apr. 1981.

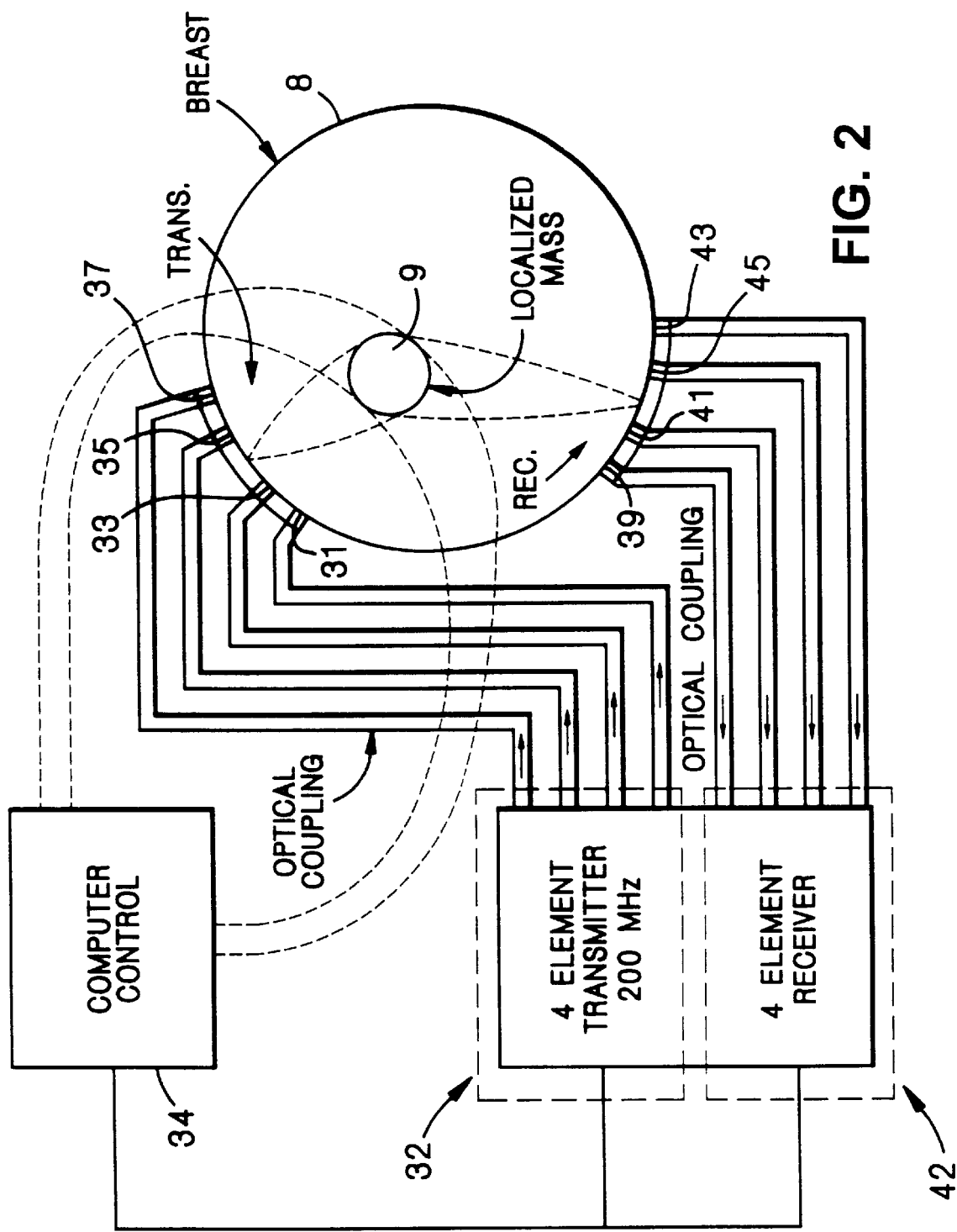

ANTIPHASE MULTIELEMENT TRANSMITTER-RECEIVER ARRAYS

ARRANGEMENT OF PHASES FOR SCAN

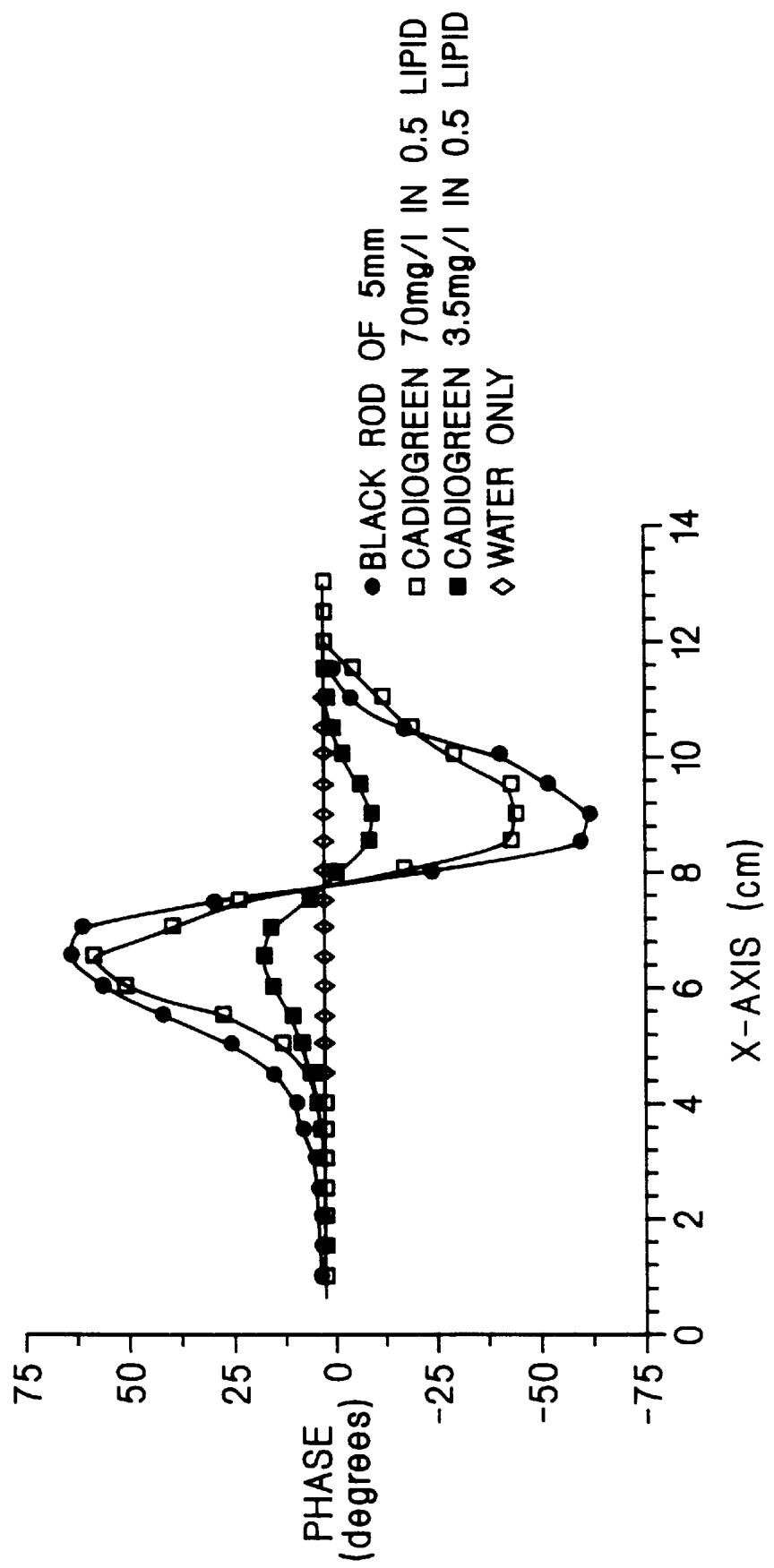

EXAMINATION AND IMAGING OF BIOLOGICAL TISSUE

This is a continuation application of a U.S. Ser. No.: 08/849,202 filed Jun. 2, 1997, now U.S. Pat. No. 5,820,558, which is a continuation of International Patent Application No. PCT/US95/15694 filed Dec. 4, 1995, which is a continuation-in-part of U.S. Ser. No.: 08/349,018 filed on Dec. 2, 1994, now U.S. Pat. No. 5,673,701. The present application is also a continuation-in-part of International Patent Application No. PCT/US93/05868 filed Jun. 17, 1993.

BACKGROUND OF THE INVENTION

This invention relates to examination and imaging of biological tissue using visible or infra-red radiation.

Traditionally, potentially harmful ionizing radiation (for example, X-ray or γ-ray) has been used to image biological tissue. This radiation propagates in the tissue on straight, ballistic tracks; i.e., scattering of the radiation is negligible. Thus, imaging is based on evaluation of the absorption levels of different tissue types. For example, in roentgenography the X-ray film contains darker and lighter spots. In more complicated systems, such as computerized tomography (CT), a cross-sectional picture of human organs is created by transmitting X-ray radiation through a section of the human body at different angles and by electronically detecting the variation in X-ray transmission. The detected intensity information is digitally stored in a computer which reconstructs the X-ray absorption of the tissue at a multiplicity of points located in one cross-sectional plane.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing; thus, it potentially causes fewer side effects. However, with lower energy radiation, such as visible or infra-red radiation, the radiation is strongly scattered and absorbed in biological tissue, and the migration path cannot be approximated by a straight line, making inapplicable certain aspects of cross-sectional imaging techniques.

Several different approaches to NIR imaging have been suggested in the past. One approach undertaken by Oda et al. in "Non-Invasive Hemoglobin Oxygenation Monitor and Computerized Tomography of NIR Spectrometry," SPIE Vol. 1431, p. 284, 1991, utilizes NIR radiation in an analogous way to the use of X-ray radiation in an X-ray CT. In this device, the X-ray source is replaced by three laser diodes emitting light in the NIR range. The NIR-CT uses a set of photomultipliers to detect the light of the three laser diodes transmitted through the imaged tissue. The detected data are manipulated by a computer of the original X-ray CT scanner system in the same way as the detected X-ray data would be.

Different approaches were also suggested by S. R. Arriadge et al. in "Reconstruction Methods for Infra-red Absorption Imaging," SPIE Vol. 1431, p. 204, 1991; F. A. Grünbaum et al. in "Diffuse Tomography," SPIE Vol. 1431, p. 232, 1991; B. Chance et al., SPIE Vol. 1431 (1991), p. 84, p. 180, and p. 264; and others who recognized the scattering aspect of the non-ionizing radiation and its importance in imaging. None of those techniques have fully satisfied all needs in tissue examination.

In summary, there continues to be a need for an improved system which utilizes visible or IR radiation of wavelengths sensitive to endogenous or exogenous pigments to examine or image biological tissue.

SUMMARY OF THE INVENTION

The invention relates to systems and methods for spectroscopic examination of a subject positioned between input and detection ports of the spectroscopic system applied to the subject.

According to one aspect, the invention features a spectroscopic system for examination of tissue of a subject, including: at least one light source of electromagnetic radiation of a visible or infrared wavelength selected to be scattered and absorbed while migrating in the tissue; at least two input ports, optically coupled to the light source, constructed to introduce at selected input locations of the examined tissue the radiation of known intensities that define a null plane in the tissue; a detection port located at a selected detection location of the examined tissue relative to the null plane; a detector, optically coupled to the detection port, constructed to detect during operation the radiation that has migrated in the examined tissue; a detector circuit connected to and receiving detection signal from the detector; the detector circuit including a sample-and-hold circuit and a subtraction circuit, both connected to the detector circuit, constructed to subtract detection signals corresponding to radiation that has migrated from a first input port to the detection port and from a second input port to the detection port, respectively, to obtain processed data; and a processor, connected to and receiving the processed data from the subtraction circuit, adapted to evaluate the examined tissue.

According to another aspect, the invention features a spectroscopic system for examination of tissue of a subject, including: a source of electromagnetic radiation of a visible or infrared wavelength; an input port, optically coupled to the light source, constructed to introduce at a selected input location of the examined tissue the radiation; a detector optically coupled to at least two detection ports located at selected detection locations defining a null plane in the examined tissue, the detector constructed to detect radiation that has migrated in the examined tissue to the detection ports; a detector circuit connected to and receiving detection signal from the detector, the detector circuit including a sample-and-hold circuit and a subtraction circuit; the detector circuit constructed to correlate emission of the radiation from the input port with detection of radiation scattered and absorbed while migrating in the tissue at the first detection port, the detected radiation being stored as a first detection signal; the detector circuit further constructed to correlate emission of the radiation from the input port with detection of radiation scattered and absorbed while migrating in the tissue at the second detection port, the detected radiation being stored as a second detection signal; the subtraction circuit constructed to subtract the detection signals; and a processor, connected to and receiving the processed data from the subtraction circuit, constructed to evaluate the examined tissue.

Embodiments of the invention may include one or more of the following additional features.

The spectroscopic system may include intensity control means constructed to regulate intensities of radiation emitted from the first and second input ports. The intensity control means may be constructed to regulate the intensities in a manner that sweeps the null plane over at least a portion of the volume of the examined tissue.

The spectroscopic system may preferably include positioning means constructed to displace the detection port to detection locations corresponding to the null plane or positioning means constructed to displace the input ports to selected locations.

The spectroscopic system may preferably include detector controller means constructed to changes the relative sensitivity of detection at the first and second detection port in order to sweep the null plane over at least a portion of the volume of the examined tissue.

Preferably, the subtraction circuit includes an analog to digital converter, connected to the sample-and-hold circuit, constructed to digitize the detection signal to produce digital detection signal, the subtraction circuit subtracting the digital detection signals corresponding to radiation that has migrated from a first input port to the detection port and from a second input port to the detection port, respectively, to obtain the processed data. The processor may preferably be further adapted to locate, in the tissue volume, a tissue region exhibiting different scattering or absorptive properties than the rest of the examined tissue volume.

The input or detection ports may be preferably arranged in a linear array. The input or detection ports may be preferably arranged a two dimensional array. The spectroscopic may preferably further include an image processor, connected to and receiving the processed data from the processor, constructed to store processed data corresponding to different combinations of input and detection ports and create image data; and a display, connected to the image processor, constructed to display the image data representing the examined tissue.

The wavelength may be preferably sensitive to an endogenous pigment of the examined tissue. The wavelength may be preferably sensitive to an exogenous pigment of the examined tissue.

In another general aspect, the invention features a scheme for spectroscopic examination of tissue including the steps of: providing at least one light source of electromagnetic radiation of a visible or infrared wavelength selected to be scattered and absorbed while migrating in the tissue, the source being optically connected to at least two input ports, and a detection port optically connected to a detector, the detector connected to a detector circuit; positioning a first input port and a second input port relative to selected input locations of a subject; selecting for each input port first and second radiation intensities to be introduced to the tissue, the selected radiation intensities defining a null plane in the tissue; positioning the detection port relative to a selected detection location of the examined tissue corresponding to the null plane, the input locations and detection location defining a volume of the examined tissue of the subject; introducing into the subject, at the first input port, radiation of the first intensity; detecting, at the detection port, the first radiation that has migrated in the examined tissue; storing, in the detector circuit, a first detector signal corresponding to the first detected radiation; introducing into the subject, at the second input port, radiation of the second intensity; detecting, at the detection port, the second radiation that has migrated in the examined tissue; storing, in the detector circuit, a second detector signal corresponding to the second detected radiation; subtracting the first detector signal from the second detector signal to obtain processed data; and examining the tissue volume using the processed data.

The spectroscopic method may further include the step of selecting the first and second radiation intensities is preferably performed in a manner that sweeps the null plane over at least a portion of the volume of the examined tissue and the step of positioning the detector to detection locations corresponding to the swept null plane.

In another general aspect, the invention features a scheme for spectroscopic examination of tissue including the steps of: providing a source of electromagnetic radiation of a visible or infrared wavelength selected to be scattered and absorbed while migrating in the tissue, the source being optically coupled to an input port, and providing at least two detection ports optically coupled to at least one detector, the detector connected to a detector circuit; positioning the input port relative to selected input locations of the tissue; positioning a first detection port and a first detection port relative to selected detection locations of the examined tissue, the locations defining a null plane in the tissue a volume of the examined tissue of the subject; introducing into the tissue, at the input port, radiation of a selected intensity and a selected wavelength; detecting, at the first detection port, radiation that has migrated in the examined tissue and storing, in the detector circuit, a first detector signal corresponding to the detected radiation; detecting, at the second detection port, radiation that has migrated in the examined tissue and storing, in the detector circuit, a second detector signal corresponding to the detected radiation; and subtracting the first detector signal from the second detector signal to obtain processed data corresponding to properties of the tissue volume.

The detecting steps may be performed in a manner that changes the relative sensitivity of detection at the first and second detection port in order to sweep the null plane over at least a portion of the volume of the examined tissue and the method may further include, simultaneously with the sweeping, positioning the input port to input locations corresponding to the swept null plane.

Further embodiments of the invention may include one or more of the following features.

The first detector signal and the second detector signal are preferably stored and subtracted in an analog form by the detection circuit. The spectroscopic method preferably further includes, before the storing steps, converting the first and second detection signals to a digital form, the subtracting step being performed digitally on the first detector signal and the second detector signal in an digital circuit.

The steps of positioning the input ports and the detection port at the respective selected locations preferably include placing the ports on the surface of the examined tissue. The steps of positioning the input ports at the respective selected locations preferably include orienting the input ports relative to the input locations thereby enabling introduction of the radiation at the input locations of the examined tissue. The step of orienting the input ports preferably include directing an optical element of the input ports to the input locations. The positioning steps are preferably performed in a manner that sweeps the null plane and the detector over at least a portion of the volume of the examined tissue.

The spectroscopic method may further include locating, in the tissue volume, a tissue region exhibiting different scattering or absorptive properties than the rest of the examined tissue volume. The method may preferably further include imaging the examined tissue including the tissue region of different scattering or absorptive properties. The method may preferably further include displaying an image of the examined tissue by utilizing to the processed data and relative locations of the input ports and the output ports.

The method may preferably further include a step of introducing an exogenous pigment into the tissue and selecting a wavelength being sensitive to the pigment.

The exogenous pigment may be preferentially accumulated in a tissue region exhibiting different scattering or absorptive properties. The exogenous pigment may be fluorescing when irradiated by selected wavelength, and the detecting steps may detect preferentially radiation wavelength of the fluorescing pigment.

In general, according to another aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; radiation pattern controller adapted to achieve selected a time relationship of the introduced patterns to form resulting radiation that possesses a substantial gradient in photon density as a result of the interaction of the introduced patterns emanating from the input ports, the radiation being scattered and absorbed in migration paths in the subject. The system also includes a detector adapted to detect over time, at a detection port placed at a selected location on the subject, the radiation that has migrated in the subject; processor adapted to process signals of the detected radiation in relation to the introduced radiation to create processed data indicative of the influence of the subject upon the gradient of photon density; and the processor (evaluation means) adapted to examine the subject by correlating the processed data with the locations of the input and output ports.

According to another aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; radiation pattern controller adapted to achieve a selected time relationship of the introduced patterns to form resulting radiation that possesses a substantial gradient in photon density as a result of the interaction of the introduced patterns emanating from the input ports, the radiation being scattered and absorbed in migration paths in the subject. The system also includes a detector adapted to detect over time, at a detection port placed at a selected location on the is subject, the radiation that has migrated in the subject; displacement means adapted to move the detection port to various locations on a predetermined geometric pattern, the various locations being used to detect over time radiation that has migrated in the subject; processor adapted to process signals of the detected radiation in relation to the introduced radiation to create processed data indicative of the influence of the subject upon the gradient of photon density; and the processor (evaluation means) adapted to examine the subject by correlating the processed data with the locations of the input and output ports.

According to another aspect of the invention, a spectroscopic system includes at least one light source adapted to introduce, at multiple input ports, electromagnetic non-ionizing radiation of a known time-varying pattern of photon density and of a wavelength selected to be scattered and absorbed while migrating in the subject, the input ports being placed at selected locations on the subject to probe a selected quality of the subject; radiation pattern controller adapted to achieve a selected time relationship of the introduced patterns to form resulting radiation that possesses a substantial gradient in photon density as a result of the interaction of the introduced patterns emanating from the input ports, the radiation being scattered and absorbed in migration paths in the subject. The system also includes at least one detector adapted to detect over time, at multiple detection ports placed at selected locations on the subject, the radiation that has migrated in the subject; processor adapted to process signals of the detected radiation in relation to the introduced radiation to create processed data indicative of the influence of the subject upon the gradient of photon density, and the processor (evaluation means) adapted to examine the subject by correlating the processed data with the locations of the input and output ports.

Preferred embodiments of this aspect of the invention include displacement means adapted to move at least one of the detection ports to another location on a predetermined geometric pattern, the other location being used to perform the examination of the subject.

Preferred embodiments of this aspect of the invention include rotation means adapted to rotate synchronously the optical input ports while introducing the resulting radiation along a predetermined geometric pattern, the input port rotation being used to perform the examination of a region of the subject.

According to another aspect of the invention, a spectroscopic system includes a light source adapted to introduce, at an input port, electromagnetic non-ionizing radiation of a known time-varying pattern of photon density and of a wavelength selected to be scattered and absorbed while migrating in the subject, the input port being placed at a selected location on the subject to probe a selected quality of the subject; detectors adapted to detect over time, at multiple detection ports placed at selected locations on the subject, the radiation that has migrated in the subject; the time relationship of the detection over time, at the detection ports, being selected to observe a gradient in photon density formed as a result of the interaction of the introduced radiation with the subject. The system also includes processor adapted to process signals of the detected radiation in relation to the introduced radiation to create processed data indicative of the influence of the subject upon the gradient of photon density, and the processor (evaluation means) adapted to examine the subject by correlating the processed data with the locations of the input and output ports.

According to another aspect of the invention, a spectroscopic system includes a light source adapted to introduce, at an input port, electromagnetic non-ionizing radiation of a known time-varying pattern of photon density and of a wavelength selected to be scattered and absorbed by a fluorescent constituent while migrating in the subject, the input port being placed at a selected location on the subject to locate the fluorescent constituent of the subject; detectors adapted to detect over time, at multiple detection ports placed at selected locations on the subject, fluorescent radiation that has migrated in the subject. The system also includes processor adapted to process signals of the detected radiation in relation to the introduced radiation to create processed data indicative of location of the fluorescent constituent of the subject, and the processor (evaluation means) adapted to examine the subject by correlating the processed data with the locations of the input and output ports.

In certain preferred embodiments, the spectroscopic system further includes an image processor, connected to and receiving the processed data from the processor, constructed to store processed data corresponding to different combinations of input and detection ports and create image data, the image data including data of the tissue region; and a display, connected to the image processor, constructed to display the image data representing the examined tissue including the tissue region.

A displacement mechanism is adapted to move synchronously the optical ports and the detection ports to another location on a predetermined geometric pattern; this other location is used to perform the examination of the subject.

The spectroscopic system also uses a wavelength sensitive to endogenous or exogenous pigments of the examined biological tissue.

The spectroscopic system also used to locate a fluorescent constituent of interest in the subject; the wavelength of the introduced radiation is selected to be absorbed in the fluorescent constituent, the detected radiation is emitted from the fluorescent constituent and processed to determine location of the fluorescent constituent.

The time-varying pattern of resulting radiation is formed by the intensity modulated radiation introduced from each of the input ports having selected phase relationship that produces in at least one direction a steep phase change and a sharp minimum in the intensity of the radiation.

The phase relationship of the introduced radiation patterns is 180 degrees.

The modulation frequency of the introduced radiation has a value that enables resolution of the phase shift that originates during migration of photons in the subject.

Other features and advantages will become apparent from the following description and from the claims.

BRIEF DESCRIPTION OF THE DRAWING

FIG. 2 is a block diagram of the phase modulation imaging system including several input ports and several detection ports in accordance with the present invention.

FIG. 9D displays the phase shifts measured for the four element array of FIG. 9A scanning absorbing objects of different absorption coefficients.

FIG. 11A shows a circuit diagram of the low frequency imaging system of FIG. 11.

DESCRIPTION OF THE PREFERRED EMBODIMENTS

Figure 1:
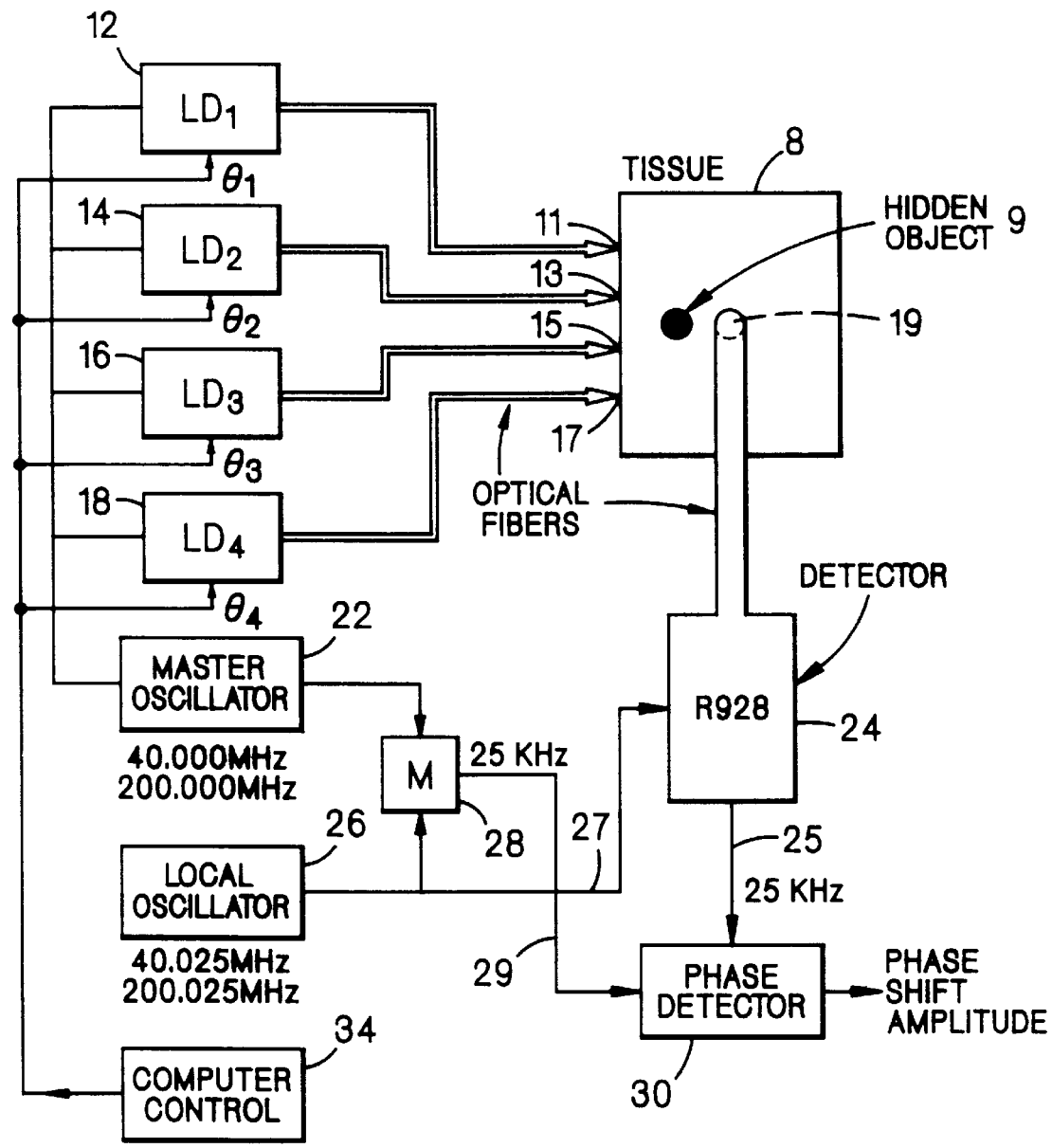
FIGS. 1 and 1A show diagrammatically a phase modulation imaging system including several input ports and one detection port in accordance with the present invention.
Figure 2A:
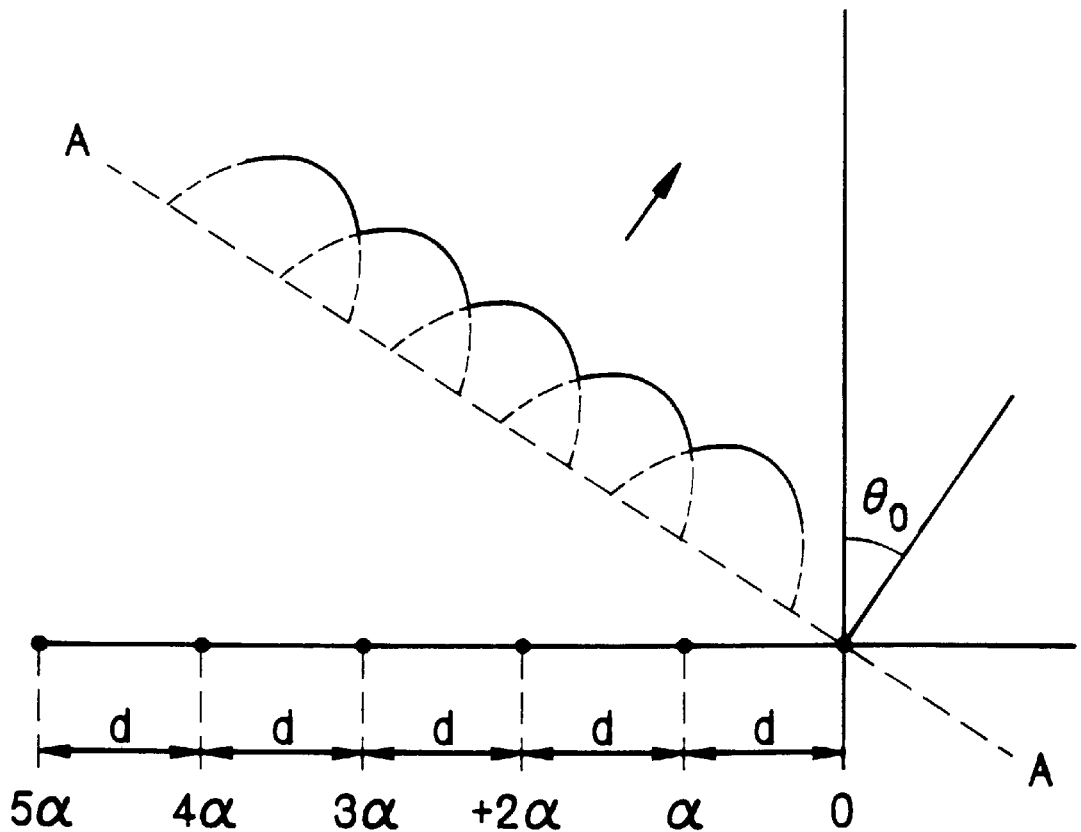
FIG. 2A depicts a phased array antenna that radiates a directional beam.
Figure 2B:
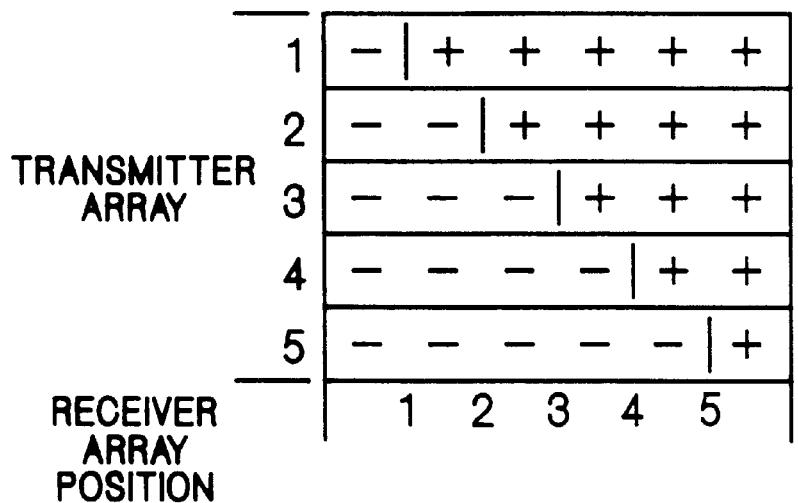
FIG. 2B depicts sequencing of the phases of an antiphase multi-element array to achieve an electronic scan of the photon density gradient in accordance with the present invention.
Figure 2B:
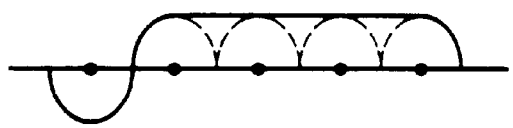
Figure 2B:
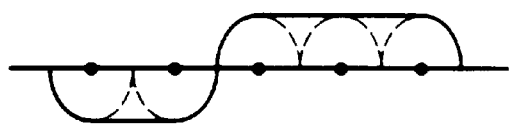
Figure 2B:
Figure 2B:
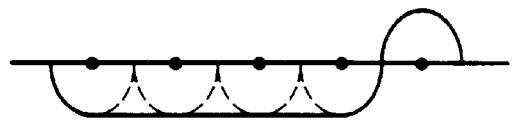
Figure 2C:
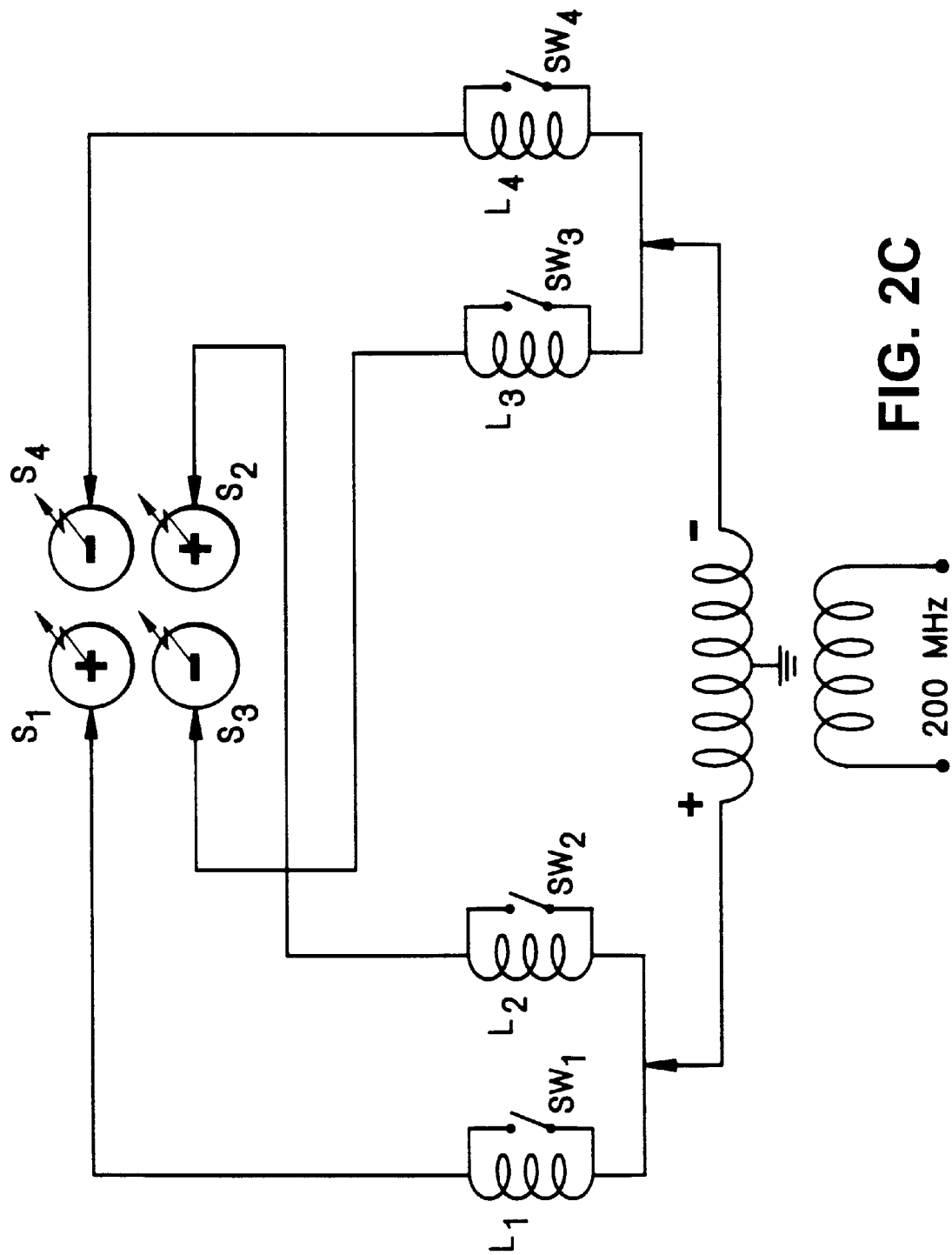
FIG. 2C depicts four element antiphased array designed for a conical scan of the photon density gradient in accordance with the present invention.
Figure 2D:
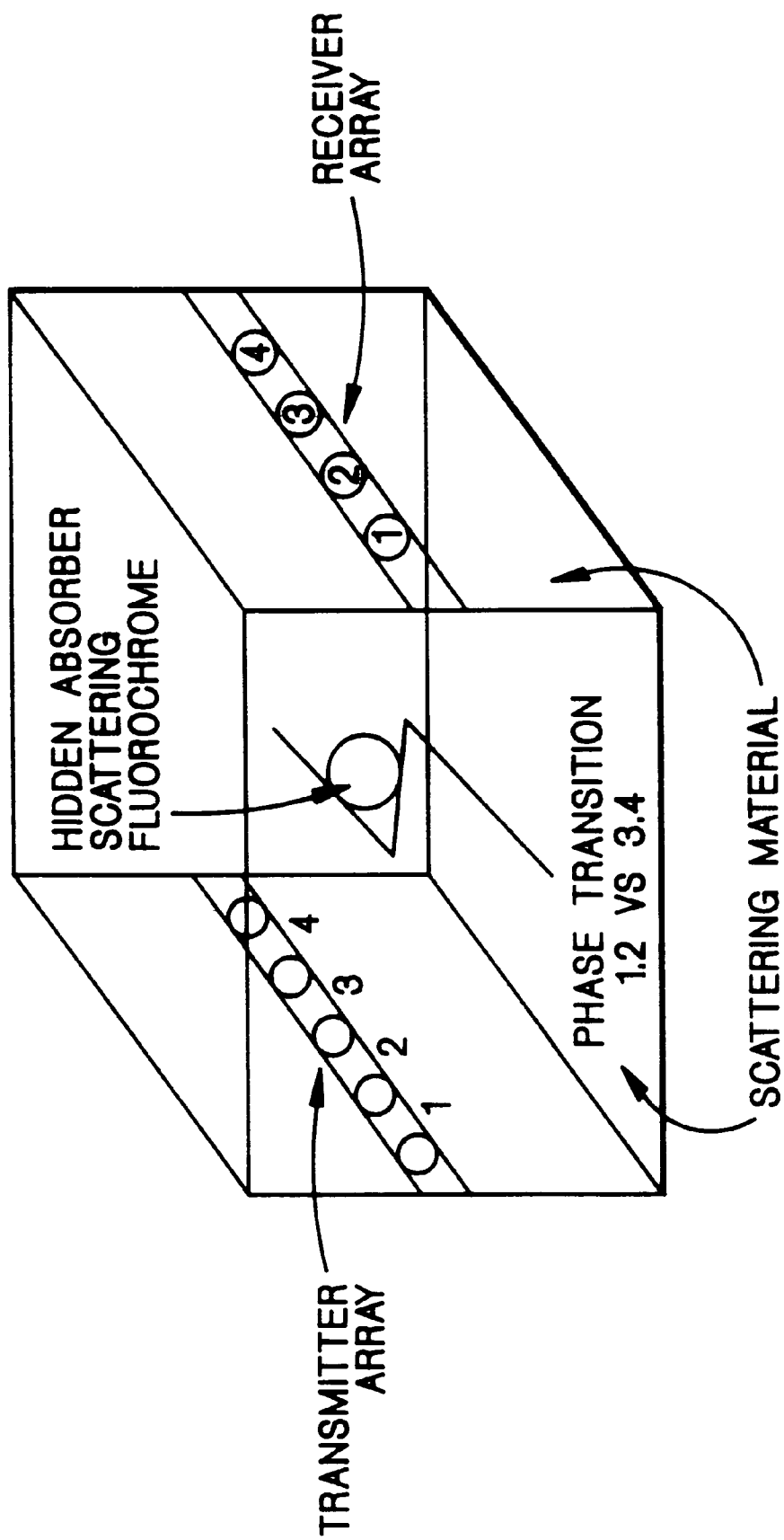
FIG. 2D depicts the input and output port arrangement of an imaging system in accordance with the present invention.
Figure 3:
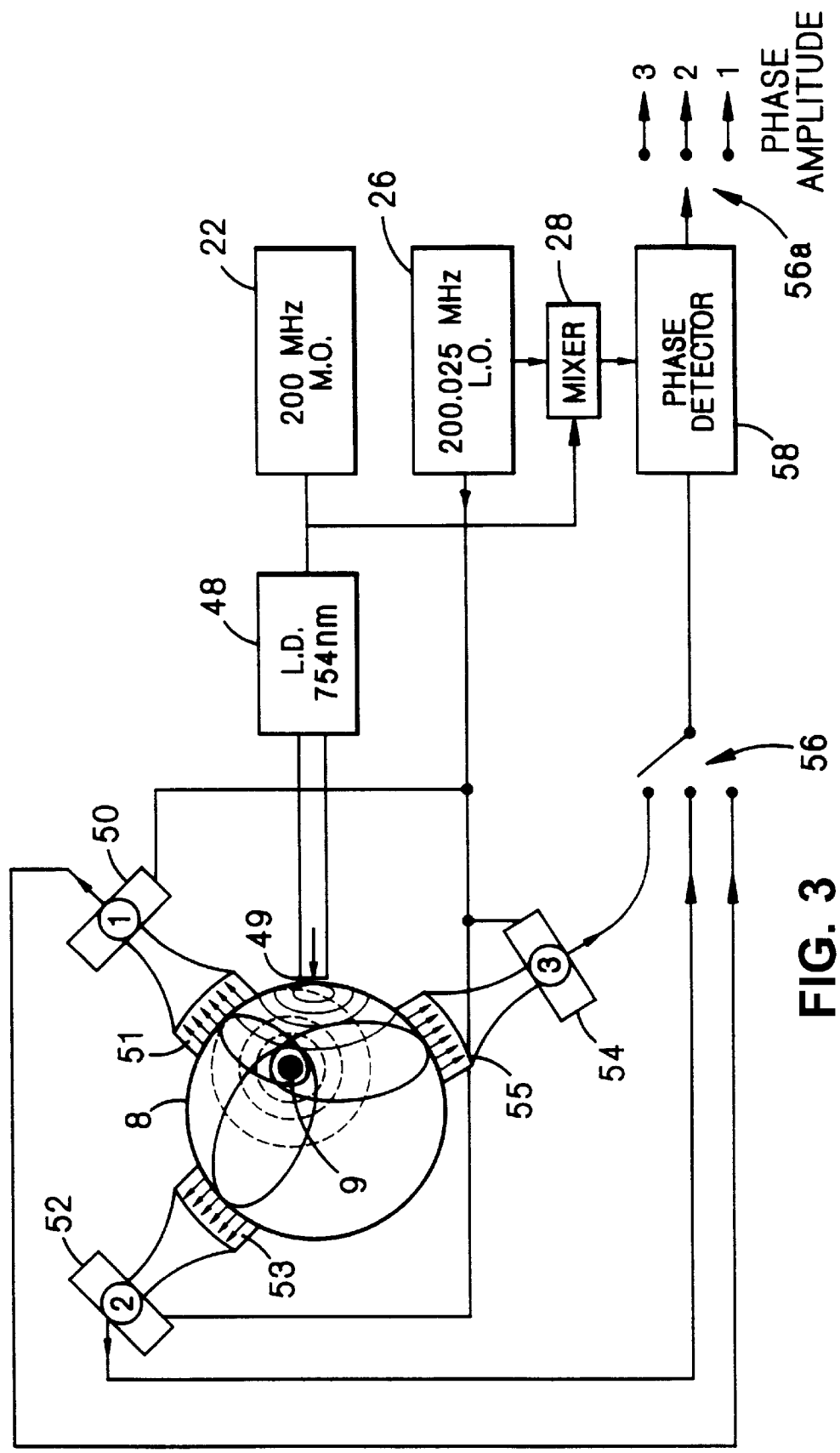
FIG. 3 depicts a phase modulation imaging system including an input port and several array detection ports in accordance with the present invention.

Imaging system embodiments of the present invention based upon interference effects of radiation migrating in a subject having scattering and absorptive properties are shown in FIGS. 1, 2, and 3. The systems effectively utilize, in this scattering medium, a directional beam of visible or IR radiation generated and/or detected by an array of sources and/or detectors, respectively. For instance, in the case of an array of sources, each source is placed at a selected location in the array and emits intensity modulated radiation, preferably coherent radiation from a laser diode, of a selected intensity and phase. The criteria for selecting the source locations, the intensities, and the phases of the respective sources is the shape of the desired beam that at any time point possesses a substantial photon density gradient produced by interference effects of radiation from the various sources. This gradient of photon density is localized and has directional properties. Overall, the resulting radiation formed by interference of the radiation of the individual sources migrates in a selected direction in the subject. In an antiphase system, the wavefront of the beam has sections of equal photon density separated by a sharp localized change in photon density. Selected different locations of the photon density gradient are shown in FIG. 2B.

In general, the wavefront propagates in the selected direction in the subject and the gradient of photon density is localized in one or more planes extending from the source array in a selected direction. If the subject includes a localized object having different scattering and absorptive properties from those of the surrounding environment, the propagating radiated field is perturbed. This perturbation is detected and from the source detector geometry the perturbing object can be located.

Figure 1A:
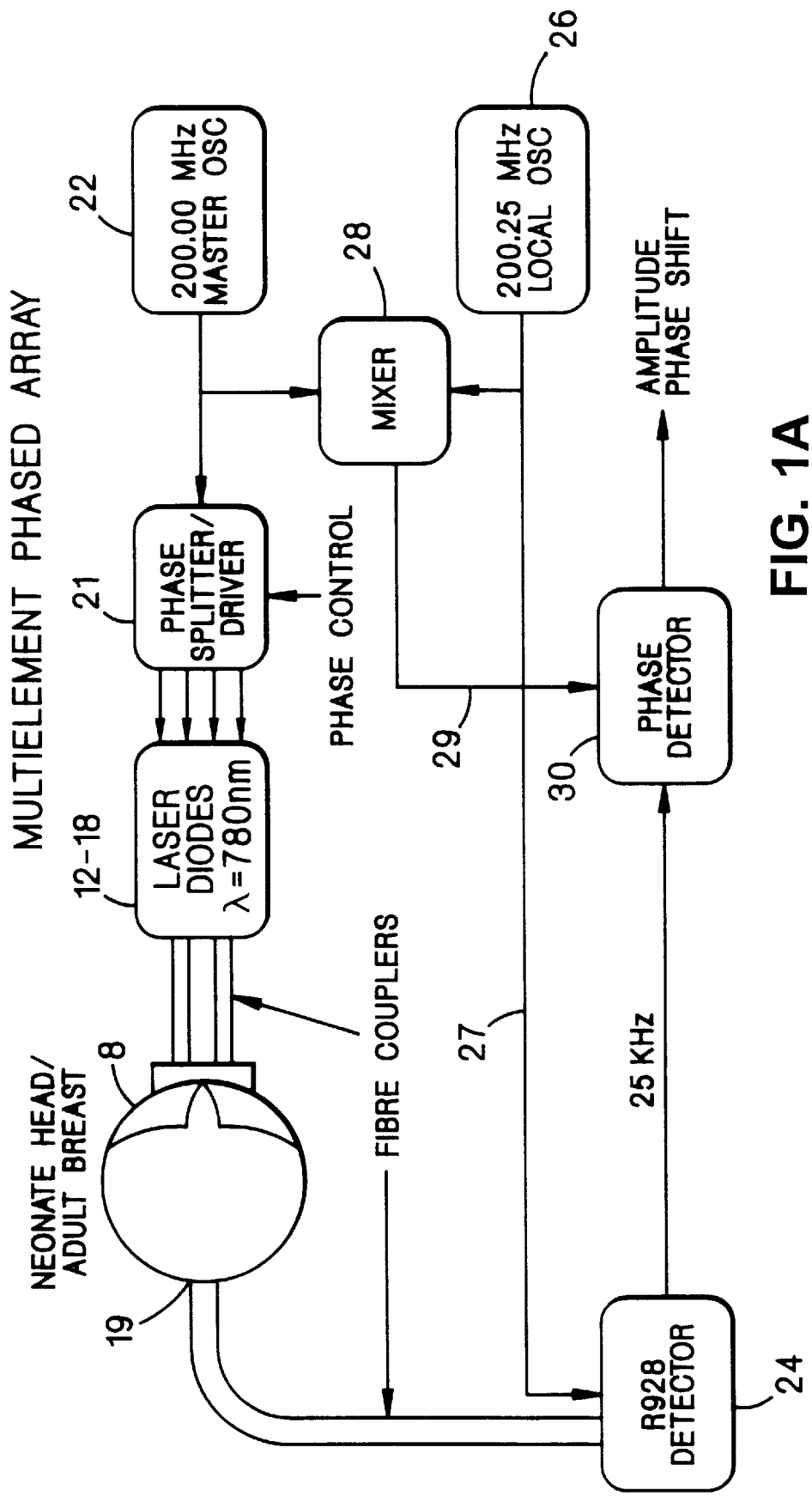

In one preferred embodiment shown in FIGS. 1 and 1A, the imaging system utilizes an array of laser diodes 12, 14, 16, and 18 for introducing light into the tissue at selected locations. The geometry of optical input ports 11, 13, 15, 17 and of an optical output port 19 is selected to examine a specific part of the tissue. From the known geometry of the optical input ports and the detection port and from the shape of the introduced and detected radiation, a computer can locate a hidden object 9 of examined tissue 8 (For example, the head or breast). A master oscillator 22, which operates at 200 MHz, excites laser diode 12 through 18, that emit light of a selected wavelength (e.g., 760 nm). The light from each laser diode is conducted to the respective input port placed on a subject via a set optical fibers. A detector 24 detects the light that has migrated through the examined tissue. Preferably, detector 24 includes a photomultiplier tube (e.g., Hamamatsu R928) powered by a high voltage supply which outputs about 900 V in order to ensure a high gain. A local oscillator 26 operating at a convenient offset frequency (e.g., 25 KHz) sends a signal to a mixer 28 and a reference signal to detector 24. Accordingly, an output waveform 25 from detector 24 is at a carrier frequency equal to the difference of the detected and reference frequency, i.e., 25 KHz.

Detector 24 (for example, PMT Hamamatsu R928 or Hamamatsu R1645u) detects the scattered and absorbed light that has migrated through the subject. Detection port 19 is located several centimeters from the location of the input ports. The PMT detector is connected to the subject by the fiber optic guide, or, alternatively, may be directly placed on the subject. It has been found that the most cost-effective detector for measuring signals of frequencies on the order of 108 Hz is Hamamatsu R928. However, the Hamamatsu R1645u detector is preferred due to its high precision. The second dynode of the PMT of detector 24 is modulated by 200.025 MHz signal 27 so that the 25 KHz hetrodyned signal 25 is received by a phase detector 30. Phase detector 30 also receives reference signal 29 from mixer 28. If phase detector 30 is a lock-in amplifier then the output signals are the phase shift and the intensity of the detected signal. Both the phase shift and the intensity of the detected light characterize the migration path of photons in the subject (e.g., the brain tissue).

Alternatively, a tunable dye laser or other laser source connected to a wide band acousto-optical modulator operating at the carrier frequency, e.g., 200 MHz can be used instead of the laser diode. The acousto-optical modulator modulates the intensity of the light emitted by the laser at the selected carrier frequency.

The invention also envisions using only one source of coherent light that irradiates one end of several optical fibers at the same time. The other end of each fiber is placed on the subject at a selected input port location. This source radiates light of a selected time varying pattern. The phase relationship and the intensity of the light carried by each fiber is varied by creating a time delay (e.g., different fiber length) and by coupling different amounts of light into each fiber.

The imaging systems of FIGS. 1, 2, and 3 are shown to have a light source of a single wavelength; however, a dual wavelength imaging system is also envisioned according to this invention. In the dual wavelength imaging system two laser diodes or a tunable wavelength laser generate light of two wavelengths that is coupled to an optical fiber. Such a system will now be described.

Figure 4:
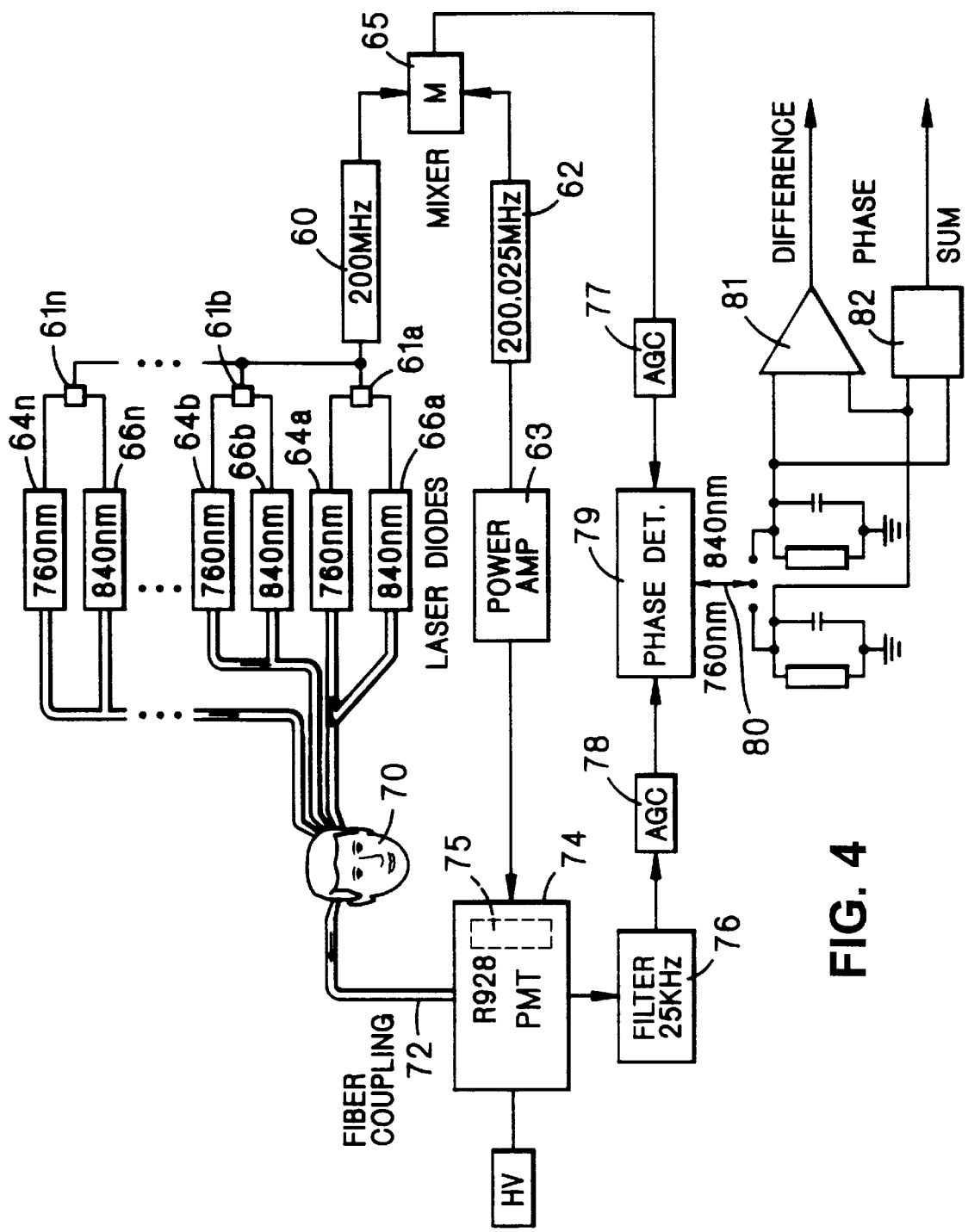
FIG. 4 is a block diagram of an alternative embodiment of a dual wavelength PMS system.

A dual wavelength operation is shown in FIG. 4. The system includes a master oscillator 60 operating at 200 MHz and an oscillator 62 operating at 200.025 MHz which is offset 25 KHz from the master oscillator frequency. The offset frequency of 25 KHz is a convenient frequency for phase detection in this system; however, other offset frequencies as high as a few megahertz can be used. Oscillator 60 alternatively drives two laser diodes 64 and 66 using switches 61, 61a, . . . These switches are driven electronically to couple a selected wavelength into the optical fiber and also to achieve a selected radiation pattern resulting from the radiation emanating from the individual fibers. An output 8 mm fiber coupler 72 collects photons for an R928 PMT detector 74. The second dynode (shown in FIG. 3B) of PMT 74 is modulated with a 200.025 MHz reference signal generated by oscillator 62 and amplified by an amplifier 63. Thus, the output signal of the PMT detector has a frequency of 25 KHz. PMT detector 74 alternately detects light of the two laser diodes that has migrated in the tissue and produces corresponding output signals, which are filtered by a filter 78 and leveled by an automatic gain control (AGC) circuit 79. A reference signal of 25 KHz is produced in a mixer 65 by mixing the 200 and 200.025 MHz oscillator signals. The reference 25 kHz signal is also leveled using the second AGC 77 and fed into a phase detector 80. Phase detector 80 generates a signal indicative of the phase of each output signal relative to the phase of the reference signal. The outputs of phase detector 80 are alternately selected by an electronic switch 82, filtered, and then input to an adder 84 and a subtractor 86 to produce sum and difference signals proportional to $<L>_{\lambda 1}+<L>_{\lambda 2}$ and $<L>_{\lambda 1}-<L>_{\lambda 2}$. The difference and sum signals are then used to calculate changes in the probed pigment and in the blood volume, respectively.

Figure 4A:
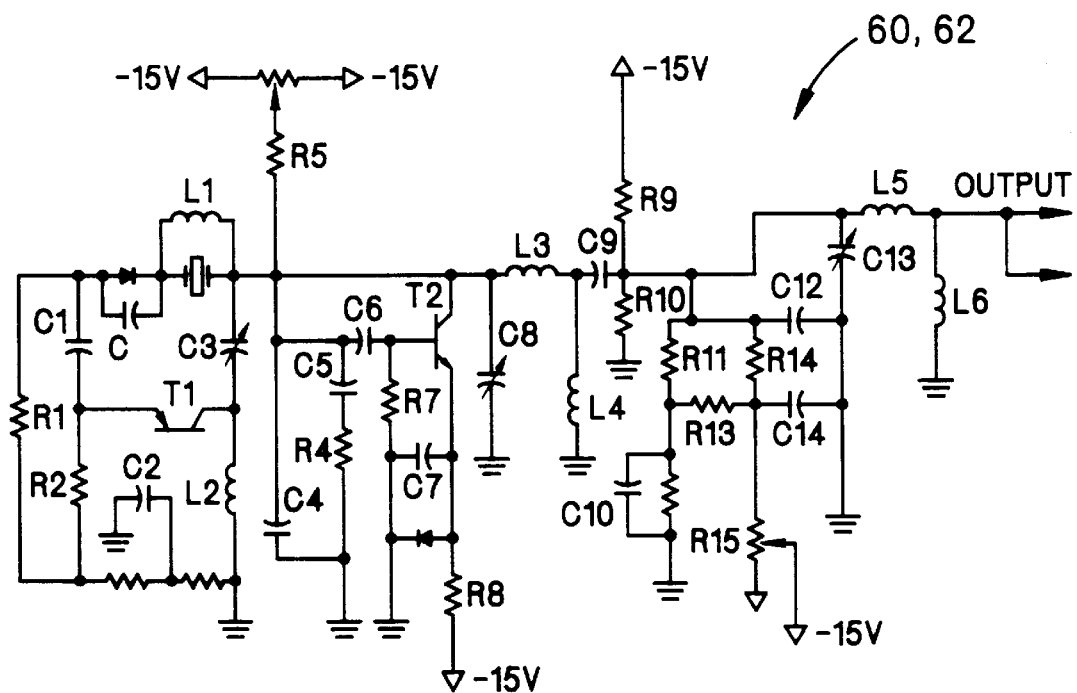
FIG. 4A is a schematic diagram of an oscillator circuit of FIG. 4.

A schematic diagram of preferred oscillator 60 or 62 is shown in FIG. 4A. This circuit has a drift of only 0.03 degrees/hr. (Weng, et al., "Measurement of Biological Tissue Metabolism Using Phase Modulation Spectroscopic Measurement," SPIE, Vol. 143, p. 161, 1991, which is incorporated herein by reference). The crystal is neutralized, which enables operation at resonance, and thus achieves long-term stability. The respective crystals of oscillators 60 and 62 are offset from each other by 25 kHz. This circuit provides a sufficient output to directly drive a 5 mW laser diode.

Figure 4B:
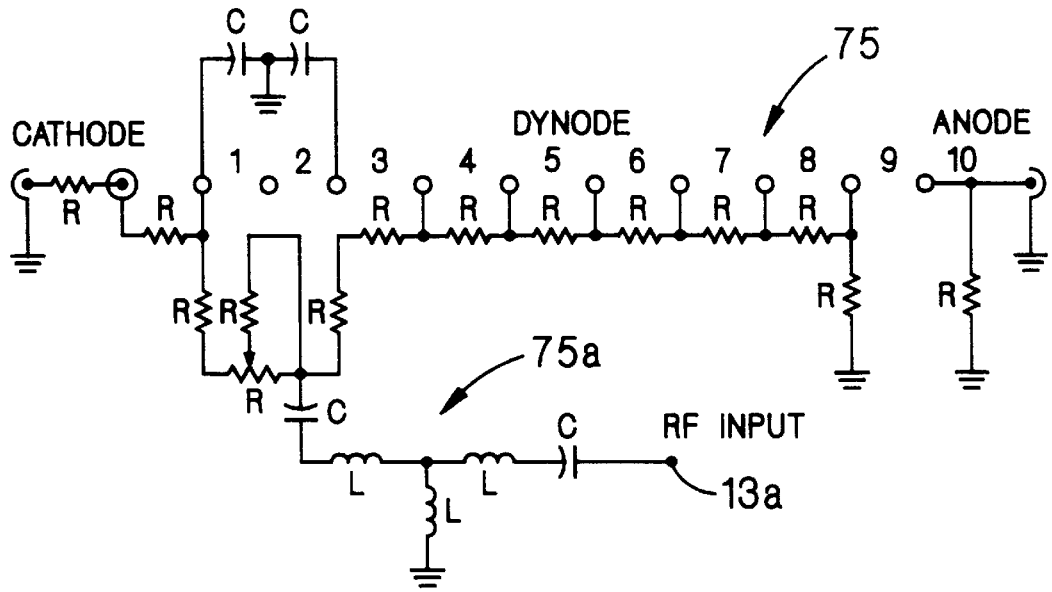
FIG. 4B is a schematic diagram of a PMT heterodyne modulation and mixing network shown in FIG. 4.

A modulation circuit 75 for the second dynode of the PMT is shown in FIG. 4B. This circuit uses a resonant circuit 75a with an impedance of 20,000 ohms instead of the usual 50Ω load with very high power dissipation, providing a 50 V drive of the photomultiplier dynode while dissipating only a few watts of power.

Figure 4C:
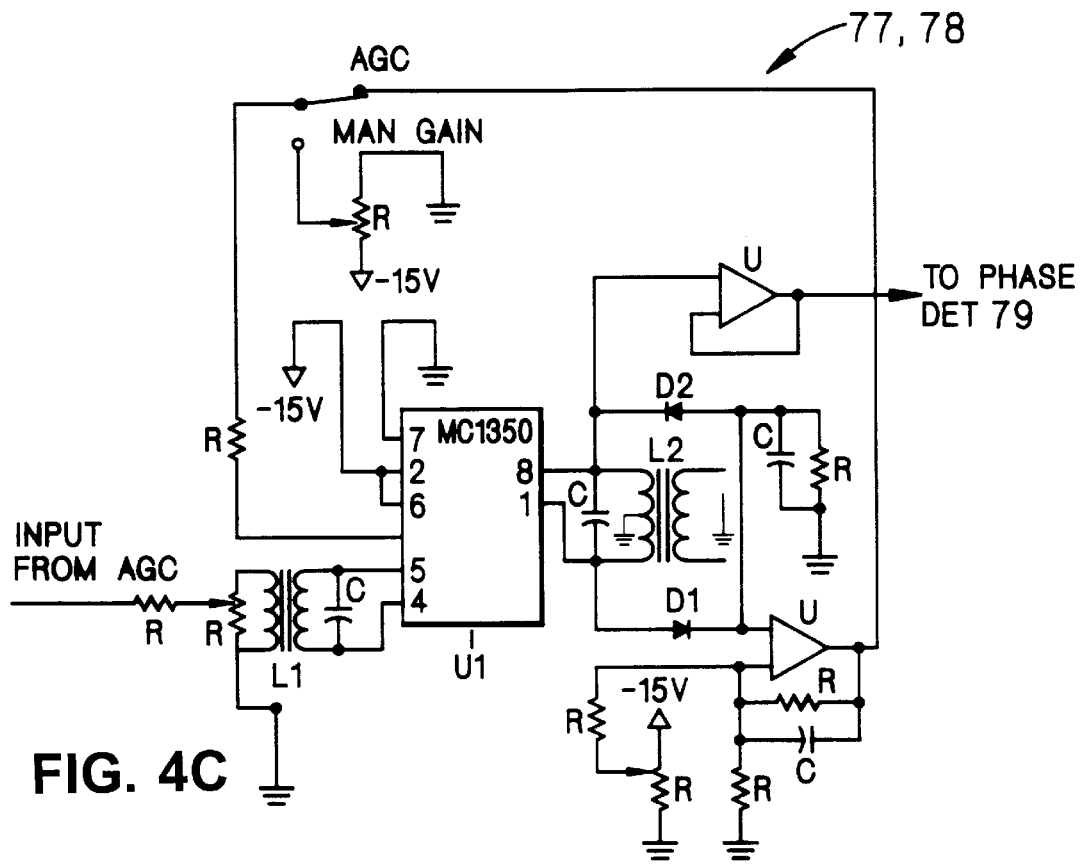
FIG. 4C is a schematic diagram of an AGC circuit shown in FIG. 4.

To obtain stable operation of the phase detector, a stable input signal is required. The 25 KHz AGC circuit 77 illustrated in FIG. 4C includes an MC 1350 integrated circuit U1, featuring wide range AGC for use as an amplifier. The signal amplitude is controlled by a feedback network, as shown. A major reason for the accurate detection of phase changes by the PMT system is that the phase detector input signal level is kept nearly constant by the AGC circuit. Since the input voltage change of between 2 and 6 volts causes variation in the phase shift of only 0.2%, the AGC circuit eliminates the need for a very stable high voltage power supply.

Figure 4D:
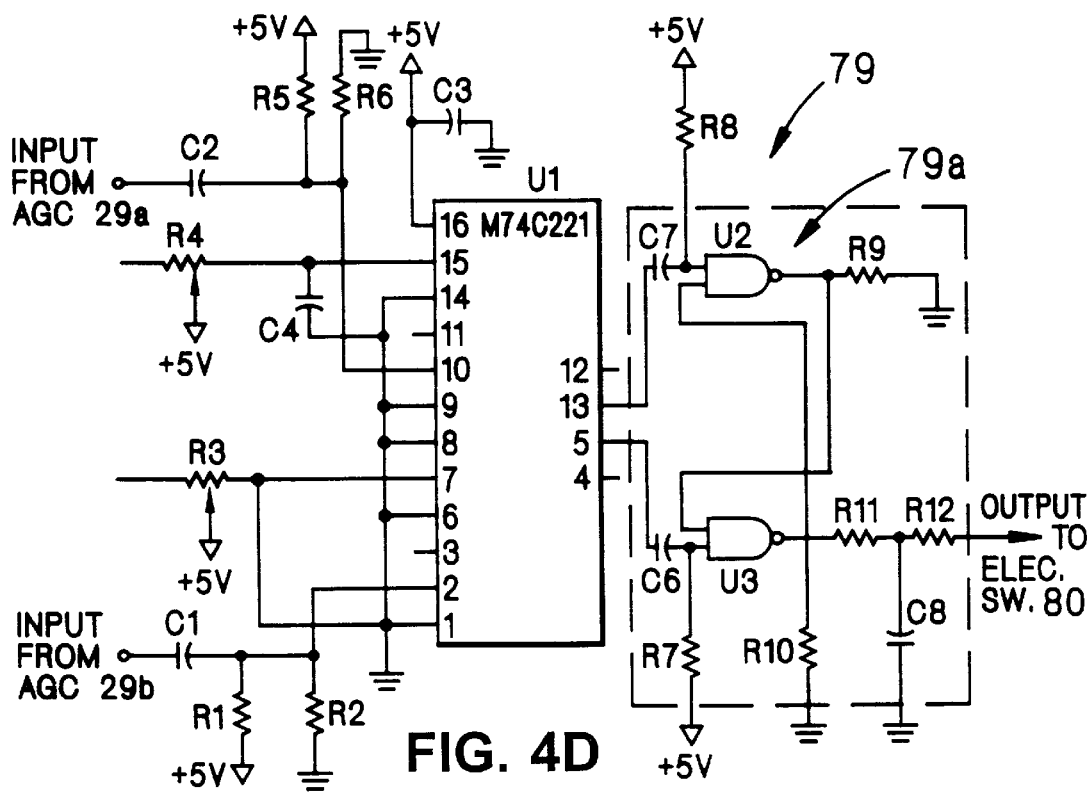
FIG. 4D is a schematic diagram of a phase detector circuit shown in FIG. 4.

A preferred phase detector circuit is shown in FIG. 4D. Two sinusoidal signals (the measurement signal and the reference signal) are transformed to a square wave signal by a Schmitt trigger circuit 80a. The phase of the square wave signal is shifted by an RC change (composed of R11, R12, C8), which makes it possible to change the measuring range. The detector further includes a 74HC221 integrated circuit. The lock-in amplifier technique obtained to derive the difference of the phase and amplitude of the two signals has the highest signal to noise ratio possible for this type of equipment.

The above-described systems utilize the carrier frequency on the order of $10^8$ Hz which is sufficiently fast to resolve the phase shift of the detected light. The characteristic time, the time it takes for a photon to migrate between an input port and an output port, is several nanoseconds. The sensitivity of the system is high, approximately 70° per nanosecond or 3° per centimeter change of pathlength, as observed in experimental models. Selection of the modulation frequency also depends on the desired penetration depth and resolution of the imaging system that will be described below. If deep penetration is desired, low modulation frequency (e.g., 40 MHz) is selected, and if shallow penetration is needed, modulation frequencies as high as $10^9$ Hz can be used.

Referring to FIGS. 1 and 1A, a master oscillator 22 operates at a modulation frequency in the range of 40 to 400 MHz selected according to the desired penetration depth of the optical field. The array of laser diodes 12, 14, 16, and 18 generates a highly directional radiation pattern, which is employed in the tissue examination.

In one preferred mode of operation, laser diodes 12 to 18 operate in a phased array pattern which is introduced into the tissue and detected by a single PMT detector 30. Master oscillator 22 operating at 200 MHz drives a multi-channel phased splitter which gives outputs at predetermined phases. Input ports 11 through 17 are located at selected distances and an appropriate phasing of the array creates a directional beam and enables scanning of the optical field in two dimensions across the tissue, as shown in FIGS. 2A, 2B, and 2D. After migrating through the tissue, the optical field is collected in a large area fiber on selected locations 19. The detected signals are heterodyned in the PMT detector 24 by utilizing the output of local oscillator 26, operating at a 25 kHz offset frequency, to detector 24. The resulting 25 kHz signal is phase detected with respect to the output signal 29 of mixer 28 and detector 24. Phase detector 30 outputs the phase and the intensity of signal 25. The detected phase shifts and intensities are stored and used for construction of an image of the subject. This is performed by computer control 34, which governs the operation of the system.

FIG. 2 depicts a phase modulation imaging system comprising an input port array for introducing radiation and detection port array for detecting radiation that has migrated in the subject. The operation of the system is controlled by computer control 34, which coordinates a transmitter unit 32 with a receiver unit 42. Transmitter unit 32 comprises several sources of visible or IR radiation adapted to introduce a selected time-varying pattern of photon density into subject 8 by array of input ports 31, 33, 35, and 37. Receiver unit 42 detects radiation that has migrated in the subject from the input port array to an array of detectors 39, 41, 42, and 47.

The radiation sources of transmitter unit 32 are intensity modulated at a frequency in the range of 40 MHz to 200 MHz, as described for the imaging system of FIG. 1. Receiver unit 42 detects and processes the radiation using the same principles of the phase and amplitude detection as described above. The signal detected at individual ports can be phased using appropriate delays.

Several modes of operation of the transmitter array and receiver array are described in FIGS. 2A, 2B, 2C, and 2D. Referring to FIG. 2A, it has been known, that for a simple horizontal linear array of N identical elements radiating amplitude modulated light spaced a distance, d, apart. The radiating wavefront is created by the interference effect. If all elements radiate in phase the wavefront propagates in a direction perpendicular to the array. However, by appropriately phasing the radiating elements, the resulting beam can scan space in two dimensions. We consider the phases of the signal along the plane A—A whose normal makes an angle $\theta_0$ with respect to the array normal. The phase of the signal from the first radiator lags the phase of the second radiator by a phase angle $(2\pi/\lambda)d \sin \theta_0$ because the signal from the second radiator has to travel a distance $d \sin \theta_0$ longer than the signal from the first radiator to reach plane A—A. Similarly, the phase of the signal from the $n^{th}$ radiator leads that from the first radiator by an angle $n(2\pi/\lambda)d \sin \theta_0$. Thus, the signals from the various radiators can be adjusted to be in-phase along the A—A plane, if the phase of each radiator is increased by $(2\pi/\lambda)d \sin \theta_0$. Consequently, at a point on the wavefront in the far field of the antenna array the signals from the N radiators will add up in phase, i.e., the intensity of the total normalized signal is a sum of the signals from the individual sources. The constructed pattern has a well defined directional characteristic and a well pronounced angular dependence, i.e., the antenna pattern has a well defined transfer characteristic of the antenna with respect to the angle $\theta_0$.

FIG. 2B depicts an arrangement of phases for the sources the system of FIG. 2 operating in one preferred mode of operation. The array of five sources is divided into two or more portions that are phased 180° apart. Each portion has at least one source. The sources of each portion radiate amplitude modulated light of equal intensity and are spaced so that the resulting beam of two or more equally phased sources has a substantially flat wavefront, i.e., no gradient of photon density. On the other hand, there is a sharp 180° phase transition, a large gradient in photon density between two antiphased portions of the array. Thus, the radiated field possesses an amplitude null and a phase transition of 180°, which is due to the large gradient of photon density.

Electronic scanning is performed by appropriately varying the apportionment of 0° and 180° phases on the sources. The five element array of FIG. 2B can have the 180° phase transition along four different parallel planes extending from the array. Scanning is achieved by electronically switching the sources by 180°, so that the photon density gradient moves in the direction parallel to the location of the sources.

Using the principles described in FIGS. 2A and 2B, a conical scan of a directional beam possessing at least one substantial photon density gradient can be accomplished using a four element antiphased array, as shown in FIG. 2C. The laser diodes are antiphased using a push pull transformer. The phasing and amplitude of four laser diodes $S_1$, $S_2$, $S_3$, and $S_4$ arranged into a two dimensional array is modified sequentially using the switches $Sw_1$, $Sw_2$, $Sw_3$, and $Sw_6$ and inductances $L_1$, $L_2$, $L_3$, and $L_4$.

FIG. 2D shows a possible arrangement of the transmitter array and the receiver array. The above described directional beam enters subject 8 at the transmitter array location and is pointed to hidden absorber 9 which perturbs the migrating beam. The field perturbation is measured by the receiver array. Scanning of the transmitter array or the receiver array is envisioned by the present invention.

A hidden absorber that includes a fluorescent constituent is detected using a selected excitation wavelength of the laser sources of the transmitter array. Then, the radiation is absorbed, and almost instantly a fluorescent radiation of a different wavelength is re-emitted. The re-emitted radiation propagating in all directions is detected by the receiver array.

FIG. 3 depicts a phase modulation imaging system comprising one input port and several arrays of detection ports. This system operates comparably to the systems of FIGS. 1 and 2. The 754 nm light of a laser diode 48 is amplitude modulated using master oscillator 22. The light is coupled to subject 8 using an input port 49. The amplitude modulated light migrates in the subject and is scattered from hidden object 9. It is also expected that hidden object 9 has a different effective index of refraction than subject 8. The migrating radiation is governed by the laws of diffusional wave optics that are described below. The scattered radiation migrates in several directions and is detected by detection systems 50, 52, and 54.

Ports 51, 53, and 55 of the detection systems can include either large area fibers or arrays if detection ports. If large area fibers are used then detector systems 50, 52, and 54 correspond to detector 24 of FIG. 1. If arrays detection ports are used, then each of detector systems 50, 52, and 54 includes several individual PMT detectors. The PMT detectors of each detector system are phased utilizing a selected phase mode, as described above. The phasing is controlled by the computer control. The detected signals are heterodyned at the PMT's and sent to a phase detector 58. Phase detector 58 detects alternatively the heterodyned signals using a switch 56. Operation of phase detector 58 is similar to the operation of phase detector 30 of FIG. 1. The detected phase and amplitude are alternatively sent to the computer control using a switch 56a. Even thought only one phase detector is shown in FIG. 3, the invention envisions use of several phase detectors.

If hidden absorber 9 includes a fluorescent constituent, laser diode 48 is selected to introduce an excitation wavelength (e.g., 754 nm). The introduced, intensity modulated radiation, excites the fluorescent constituent which re-emits radiation in all directions, as shown in FIG. 3. The re-emitted radiation is detected using detector systems 50, 52, and 54. To increase the system resolution, each detector can be furnished with an interference filter selected to pass only the fluorescent radiation.

The interference of several waves, as described in FIG. 2A, has been long known in a non-scattering medium, wherein the radiation propagates on a straight line, but not in a strongly scattering medium. Referring to FIGS. 6, 6A, 6B, and 6C, in a simple experiment, interference of two different diffusive waves in a strongly scattering medium was demonstrated. Propagation of visible IR radiation in a scattering medium such as tissue can be described by diffusion of photons, and thus we describe it as a diffusive wave.

Figure 6:
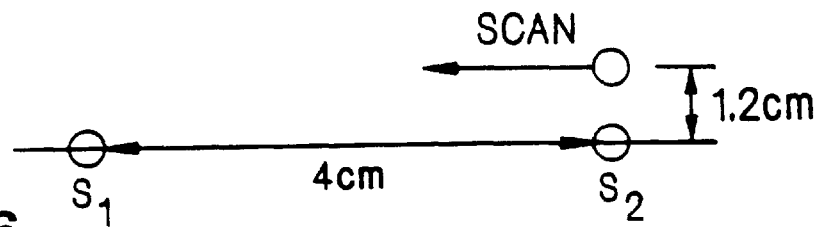
FIG. 6 shows an experimental arrangement of a two element phased array used in an interference experiment.
Figure 6A:
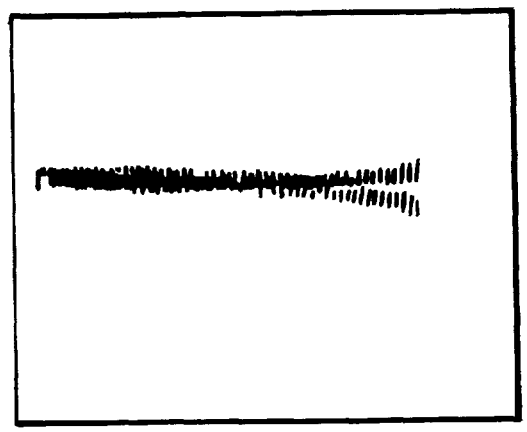
FIGS. 6A, 6B, and 6C show detected interference patterns of two diffusive waves.
Figure 6B:
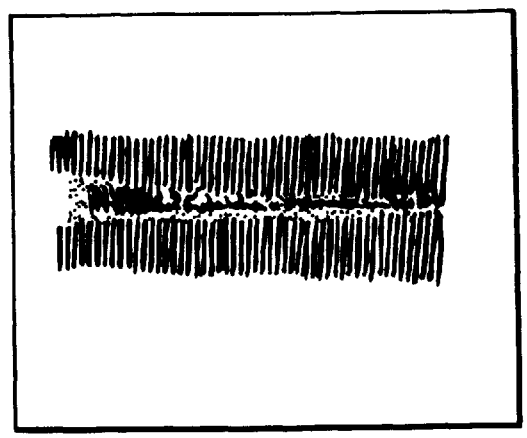
Figure 6C:
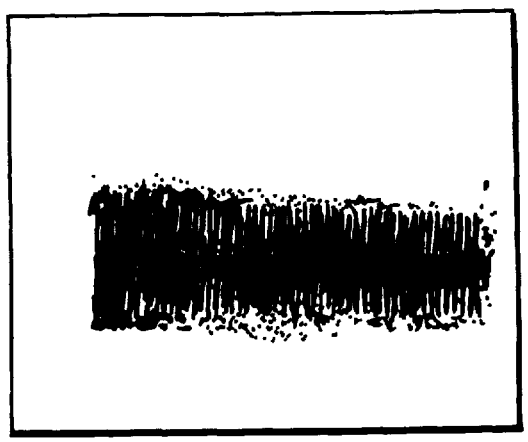
Figure 7:
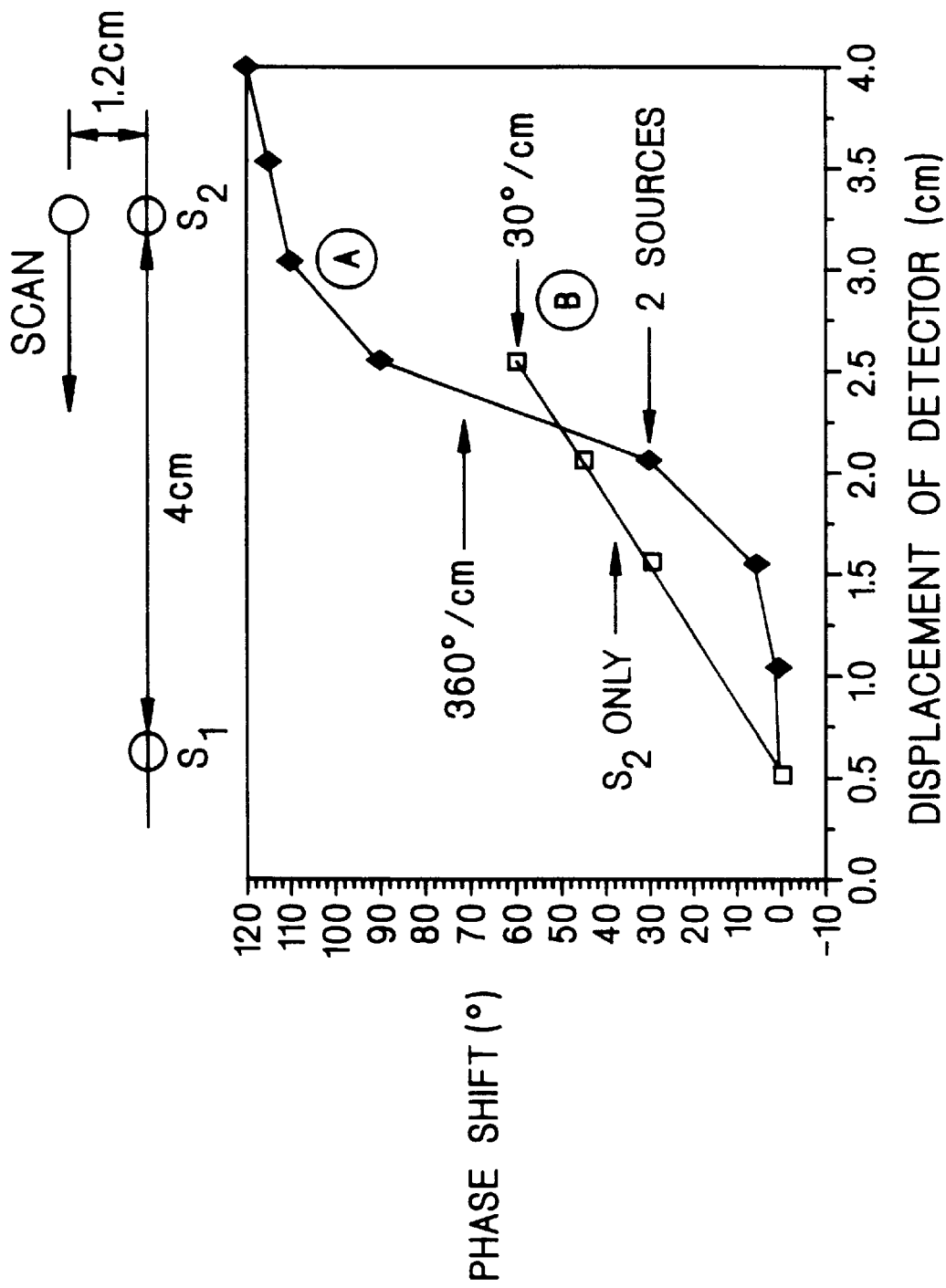
FIG. 7 displays the phase shifts measured for a two element array (curve A), and for a single source (curve B).

Referring to FIG. 6, the two laser diodes were separated at a distance of 4 cm and 1.2 cm from the detection port. The intensity modulated light of the two laser diodes at frequency 200 MHz was sent through two optical fibers to a container with an Intralipid™ suspension. The source detector distance was varied by moving the optical port of the detection fiber along a line parallel to the position of the sources. FIGS. 6A, 6B, and 6C show measured maxima and minima of the optical field migrating in the medium. This data demonstrates interference between two diffusive waves created by two coherent emitting sources of phase difference 180 degrees. FIG. 7 summarizes the experiment, wherein the displacement of the detector is plotted against the phase shift measured by the detector. The phase shift displays the steepest part of the trace, curve A, (slope of about 360°/cm) at the displacement of about 2.25 cm. Curve B is measured with an optical field of source $S_2$. Here, the measured slope is about 30°/cm. When comparing curves A and B we demonstrate much higher sensitivity of the null detection of the two element array contrasted with a diminished sensitivity to the detector displacement when using a single source arrangement. The sensitivity of the two source arrangement is increased by about a factor of 10. The sensitivity is further increased when using four or more element phased array, which sharpens the photon density gradient and thus provides a higher resolution for locating the hidden object.

In a strongly scattering medium, the emitted photons undergo a large number of collisions and their migration can be determined by applying the diffusion equation. The diffusion equation for photons in a uniformly scattering medium was solved by E. Gratton et al., "The possibility of a near infrared optical imaging system using frequency domain methods." in Mind Brian Imaging Program, Japan 1990; and by J. Fishkin et al., "Diffusion of intensity modulated near-infrared light in turbid media", SPIE Vol. 1413 (1991) p. 122. A solution of the diffusion equation was obtained for the light of a point source (at r=0) radiating $S(1+M \exp[-i(\omega t+e)])$ photons, wherein S is the source strength (photons/sec.), M is the modulation of the source at frequency $\omega$, and e is an arbitrary phase. The photon intensity can be calculated as $$I(r,t)=c^* \rho(r,t),$$

wherein $\rho(r,t)$ is the photon density and $c=10^8$ m/s is the velocity of light.

When solving the diffusion equation using a spherical-harmonics approximation in a non-absorbing medium for the density of photons $\rho(r,t)$ than $$I(r,t)=(I_0/Dr)+(I_0/Dr)\exp[-r(\omega/2cD)^{1/2}]\times\exp[ir(\omega/2cD)^{1/2}i(\omega t+e)],$$

wherein the diffusion constant D is ½ of the mean free path. In the absence of an amplitude modulated signal ($\omega=0$) the solution corresponds to a spherical wave propagating without attenuation. For a non-zero frequency, the amplitude of the signal at a frequency $\omega$ decreases exponentially. The light wave front the emitted advances at the constant velocity V $$V=(2Dc\omega)^{1/2}$$

and has wavelength $$\lambda=2\pi(2cD/\omega)^{1/2}$$

The above equations show that higher modulation frequencies yield shorter effective wavelengths, and smaller diffusion constants also give shorter effective wavelengths. In principle, short wavelengths can be obtained using high frequency modulated waves in a very turbid medium. However, the amplitude of the modulated wave decreases exponentially with the modulation frequency. Therefore, the best resolution, i.e., the shortest wavelength, is obtained using the highest frequency which still gives a measurable signal. The diffusion process limits the penetration depth at any given modulation frequency, because of the exponential decrease of the wave's amplitude, and also decreases the velocity of light propagation.

The above described diffusion wave approach treats amplitude modulated light waves in scattering media using the framework of wave optics. The photon intensity, calculated as superposition of different waves, constitutes a scalar field, propagating at a constant velocity. At any given modulation frequency, the wave optics phenomenology of scalar fields is valid. Therefore, in the frequency-domain, the measurement and analysis of light diffusing in tissues from several sources will undergo constructive and destructive interference. Furthermore, wave refraction occurs at a boundary between two different tissues. It causes a deviation of the direction of propagation of the wave front, and thus there is a change in the amplitude and phase shift of the propagation wave. The direction change is a function of the ratio of the effective index of refraction in the two tissues. In diffusional wave optics, on the other hand, the wave's amplitude is exponentially attenuated as the wave propagates in the scattering medium. This attenuation is in addition to the exponential attenuation caused by finite absorption of the medium.

Amplitude modulated waves propagate coherently in the scattering medium; this is crucial for image reconstruction. It is possible to accurately measure in real time, the average intensity, amplitude, and phase of the wave front over a large area using a single detector or an array of detectors applying well-established frequency-domain methods.

The emitters are varied sequentially in phase starting with the first emitter in the line and followed by subsequent emitters. Each emitter emits a spherical wave and propagation of the resultant beam is perpendicular to the wavefront. If all the transmitter delays are equal, the beam travels straight ahead. Delay lines which produce variable transmitter delays can be used to obtain appropriate phasing for steering the beam across the tissue. The same principle can apply during reception.

There are two important aspects of imaging as envisioned by the present invention. The first is a geometrical aspect and the second is phasing of the transmitters and receivers.

It is also possible to construct a two-dimensional array for two-dimensional pointing (e.g., FIG. 2C). The multiplexing switches used with these arrays can be constructed as an integral part of the array and can consist of field effect transistors arranged so that access to any element may be obtained by the application of two adverse signals.

In addition to electronic scanning, the two-dimensional scanning can be achieved by moving the array of sources and detectors in a regular pre-determined pattern in a plane parallel to that being investigated in the subject. For maximum detection, the detector is places in the plane of the photon density gradient of the resulting field created by the array of sources. The plane of the photon density gradient is swept as the array moves. In this sweeping action, as a strongly or weakly absorbing object enters the radiation field, the detector registers a field imbalance due to the above described refraction of the propagating radiation. A two-dimensional image is formed by storing the information while the probe is moved across the subject. Several scans in different imaging planes are envisioned by the invention. If the system is duplicated or time shared in two other faces of a cube, an algorithm would be used to provide a 3-dimensional picture of the object by triangulation, as known in the art. The data storage is accomplished electronically.

The detector detects the intensity and the phase shift of the radiation that has migrated in the subject. The phase shift depends on the tissue properties, i.e., absorption and scattering. For the low frequencies the phase shift is proportional to $((1-g)\mu_s/\mu_a)^{1/2}$ and for the high frequencies proportional to $1/\mu_a$. To obtain desired penetration depth, appropriate frequency for both master oscillator 22 and local oscillator 26 is chosen; however, the phase relationship of the laser diodes is maintained.

Different types of phased arrays are designed for optimal examination and imaging of different human organs (e.g., human head or breast). The amplitude and phase of the signals can be monitored on a precision oscilloscope. In order to scan the phased array past a fixed object of approximately known position, as in needle localization procedures, the location of the input and output ports will be scanned past the object and the position of maximum phase shift will be recorded in one-dimension; however, detection in two and three dimension can be performed in the same way.

Figure 8A:
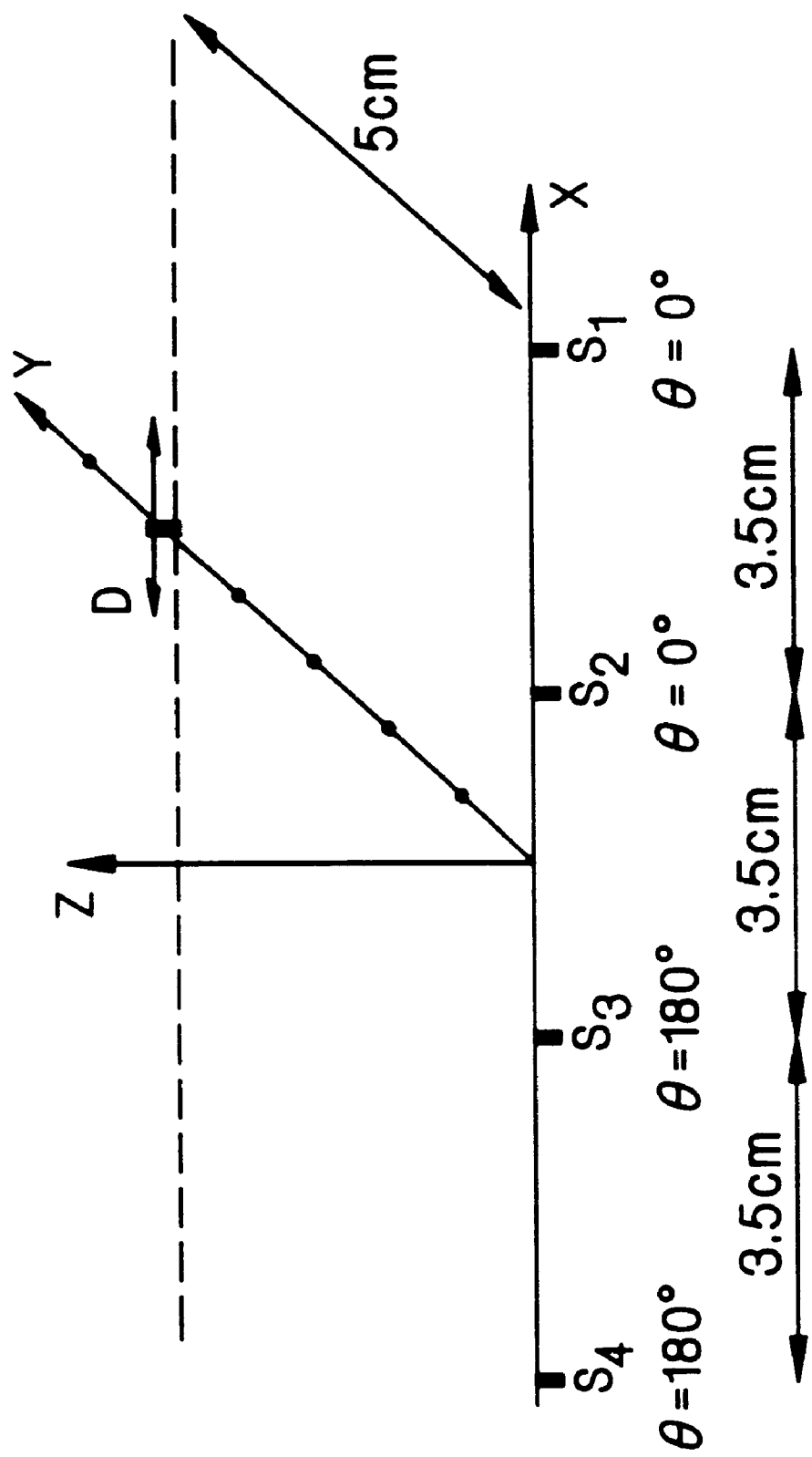
FIG. 8A depicts an experimental arrangement of sources of a four element phased array and a detector.
Figure 8B:
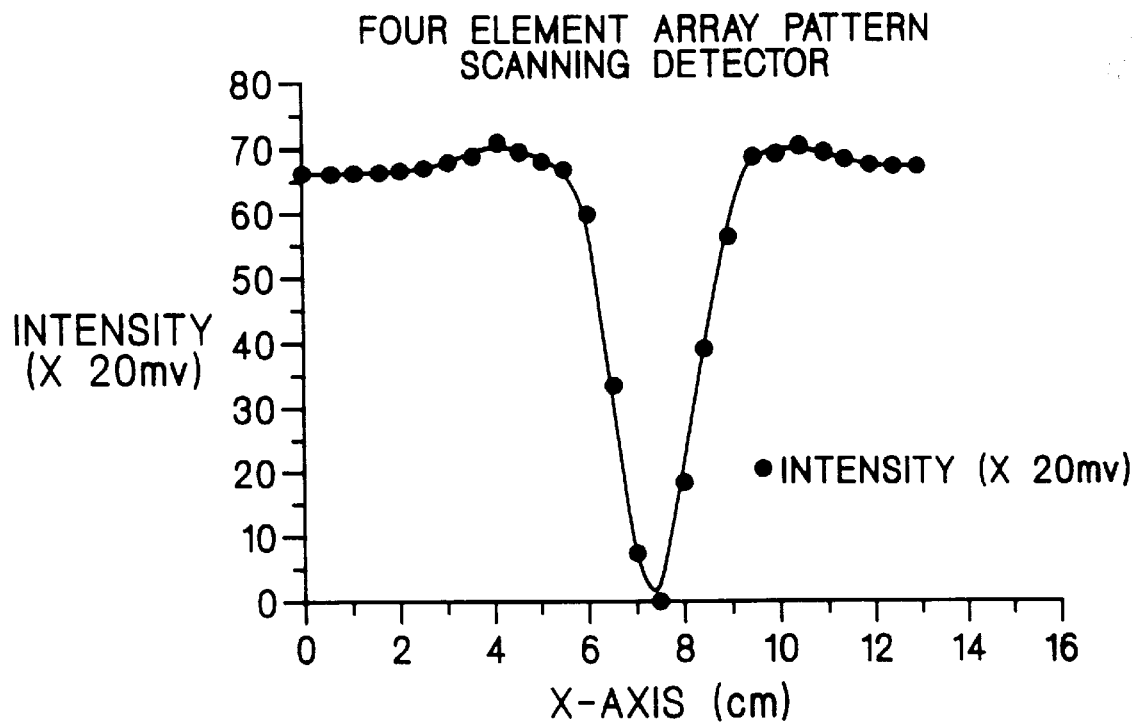
FIGS. 8B and 8C display the intensities and the phase shifts measured for the four element array of FIG. 8A, respectively.
Figure 8C:
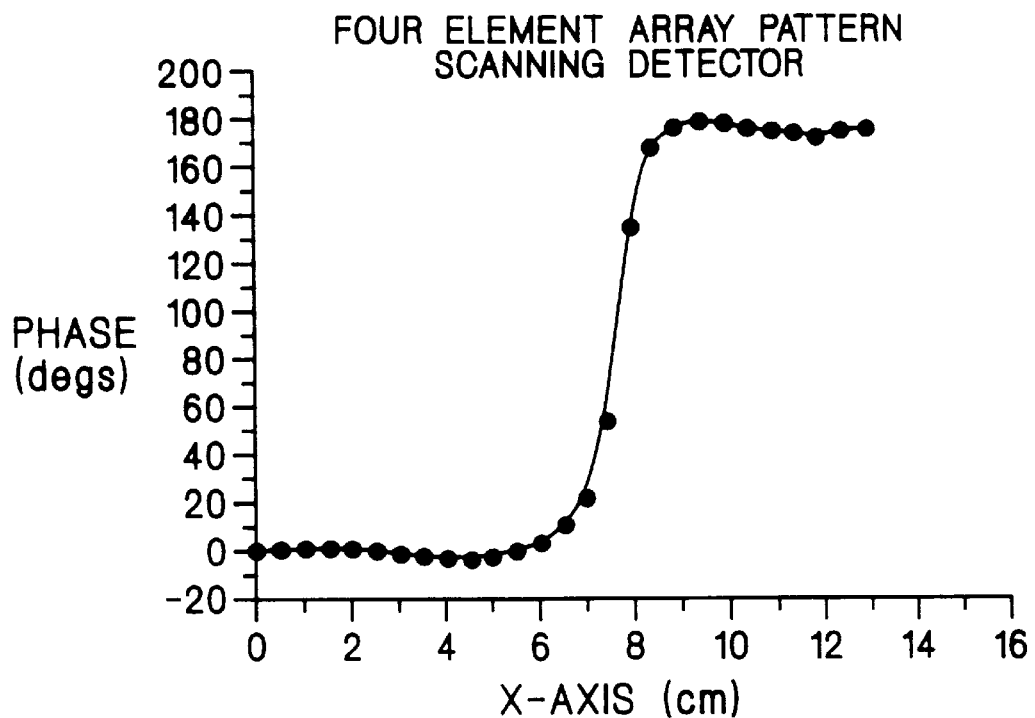

In the preferred mode of operation, the array of sources is phased 180° apart, as shown in FIG. 8A. There is a sharp 180° transition of photon density wave, a large gradient in photon density, from $S_2$, $S_2$ sources to the $S_3$, $S_4$ sources. Thus, the radiated field gives an amplitude null and a phase transition of 180° corresponding to the y-z plane, i.e., perpendicular to the detector. If a larger number of similarly phased sources is used, the transitions are even sharper. The array produces a uniform photon density pattern on each side of the array, as shown in FIGS. 8B and 8C. If an absorbing object is placed in this directional field of diffusing optical waves, imbalance in the photon density is measured. The detection of a hidden object is accomplished by translating the experimental transmitter-receiver system of FIG. 8A.

In addition to the mechanical scanning achieved by moving of the input-output port system, electronic scanning can be performed using the multiple source and multiple detector system of FIG. 2. As shown in FIG. 2B for an array of five sources, there is a 180° phase transition in the resulting migrating field due to the 180° phase difference between the antiphased sources radiating amplitude modulated light. The plane of the 180° phase transition can be shifted in parallel by appropriately varying the apportionment of 0° and 180° phases on the sources. This is performed by sequentially switching the phase of the sources by 180°. In each case, the detection port located on this plane is used for collecting the data. As the sources are electronically switched by 180°, the detection array can be also electronically switched from one detection port to another. The signal from the receiving optical fiber is coupled to one shared PMT detector. However, the system can also include several detectors. If the systems of FIGS. 1 or 1A are used, the electronic source scanning can be combined with synchronous mechanical movement of the detection port.

In general, the invention utilizes the photon density gradient created in the migrating field since it increases the resolution of the detection. As known to one skilled in the art, the photon density gradient formed by interference effects of the individual wave can be created not only by appropriate phasing of the sources but also by other methods such as appropriately spacing the sources, creating an imbalance in the radiated intensity of the individual sources, and other.

FIG. 8A shows the arrangement of the input ports 11 to 17 and detection port 19 of FIG. 1. As described above, light of each laser diode 12 through 18 is intensity modulated at the 200 MHz frequency. Wavelength of the intensity modulated radiation is $$\lambda = \left(\frac{4\pi c/n}{3f\mu_s}\right)^{\frac{1}{2}}$$

wherein f is the modulation frequency of 200 MHz, $\mu_s$ is the scattering factor which is approximately 10 cm$^{-1}$ in an Intralipid™ solution with refractive index n, and c is 3×10$^8$ cm/s. Thus, the expected wavelength is about 7 cm.

The input ports $S_1$, $S_2$, $S_3$, and $S_4$ are set 3.5 cm apart and are anti-phased by 180° using a push pull transformer. The antiphased array creates a large gradient in photon density chosen to take advantage of the destructive interference with the null detection. The laser diodes emitting 754 nm light are intensity modulated at 200 MHz using master oscillator 22, and the local oscillator 26 is operating at 200.025 MHz to perform the dynode modulation of PMT detector 24. The detected intensities and phase shifts of an x-direction scan (FIG. 8A) of detection port 19 are plotted in FIGS. 8B and 8C, respectively. As expected, the intensity has a sharp minimum in between sources $S_2$ and $S_3$ where the phase is changed 180°. The peak width at half maximum is about 2 cm. In addition to the x-direction scan of the detection port, the detection port was scanned in y-direction wherein, as expected, no variation was observed.

Figure 9A:
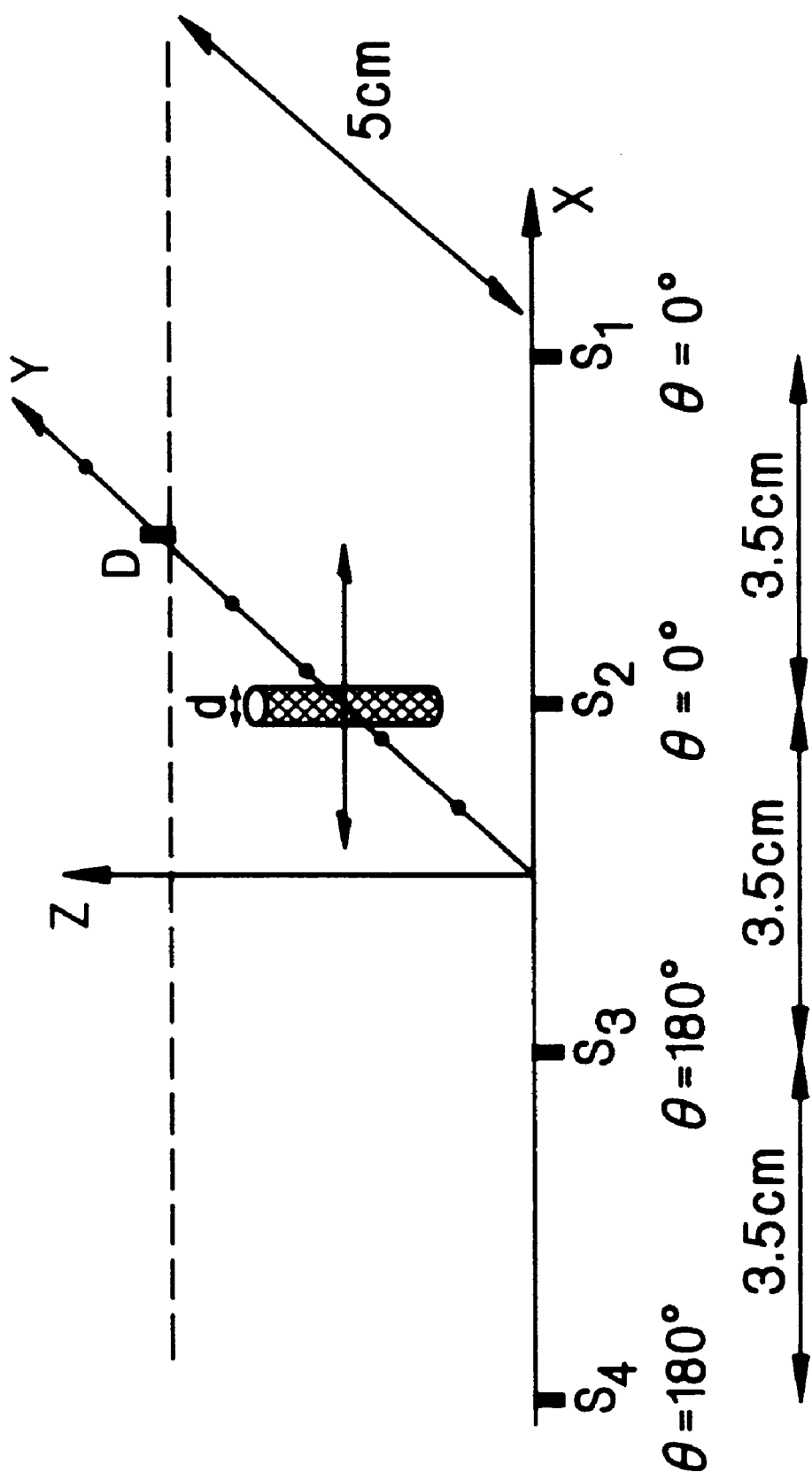
FIG. 9A depicts an experimental arrangement of sources of a four element phased array, a detector, and a strongly absorbing object.
Figure 9B:
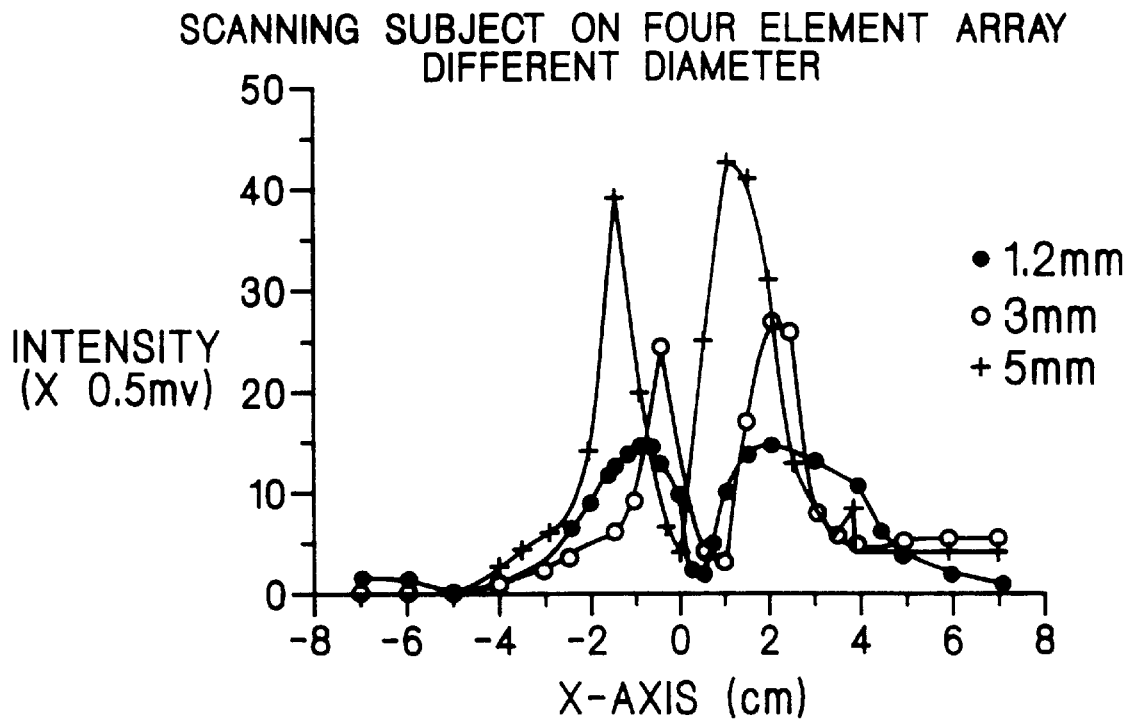
FIG. 9B, 9C display respectively the intensities and the phase shifts measured for the four element array of FIG. 9A scanning absorbing objects of different sizes.
Figure 9C:
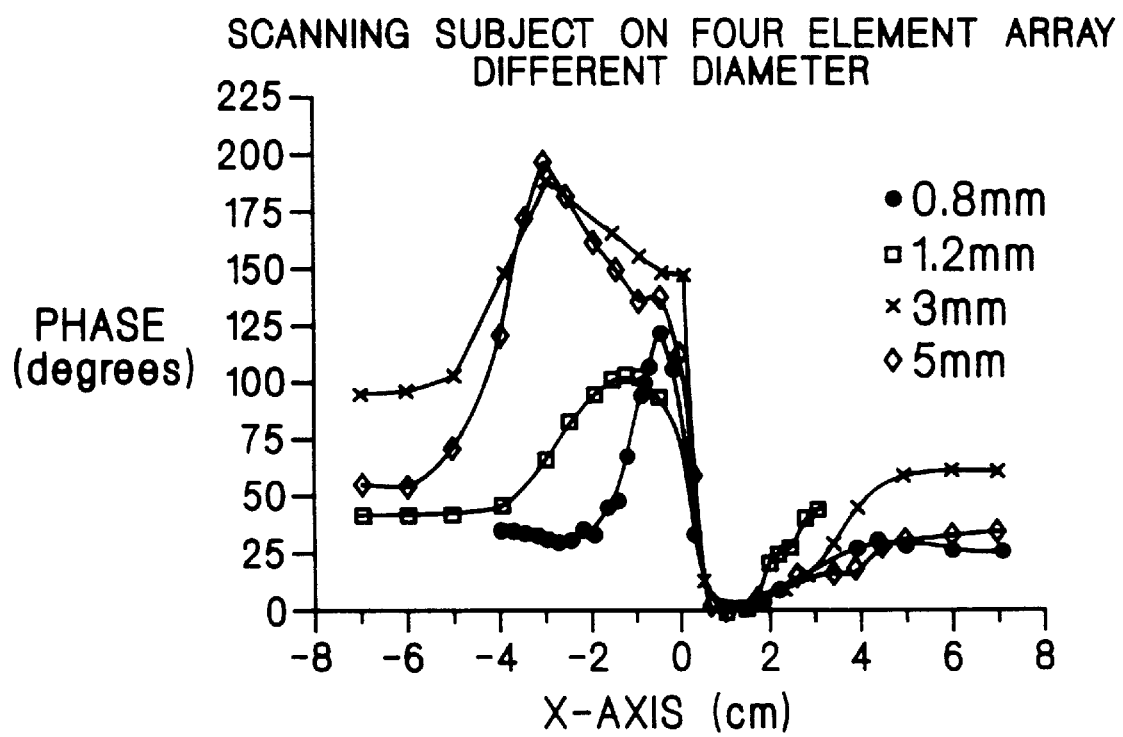

Referring to FIG. 9A, cylindrical objects of different diameter, d, were scanned using the previously described phased array. The objects were placed in the middle of the linear array displaced 2.5 cm from the x-axis. The detection port was located on the x-axis and each object was moved parallel to the x-axis at the 2.5 cm y displacement. The intensity and phase shift detected at different locations are plotted in FIGS. 9B and 9C, respectively. The intensity pattern for each moving object has two maximum and one minimum when the scanned object was located at x=0, y=2.5 point during its scan along the x-axis. At this point, a large phase change is detected, as shown in FIG. 9C. The phase detection has inherently larger resolution of a localized absorber; a hidden object of size as small as 0.8 mm can be detected.

The response due to different absorption of the hidden object was studied using a 5 mm cylinder of different absorption coefficient scanned by the 4 element phased array of FIG. 9A. The detected phase change is shown in FIG. 9D. The 5 mm black rod displays the largest phase change due to its high absorption, and the cylinder filled with cardiogreen 3.5 mg/l which has absorption coefficient $\mu_a$=200 cm$^{-1}$ shows the smallest phase change. In scanning of a hidden object, these experiments correspond to mechanically displacing the source detector system, or electronically scanning the subject.

Figure 10A:
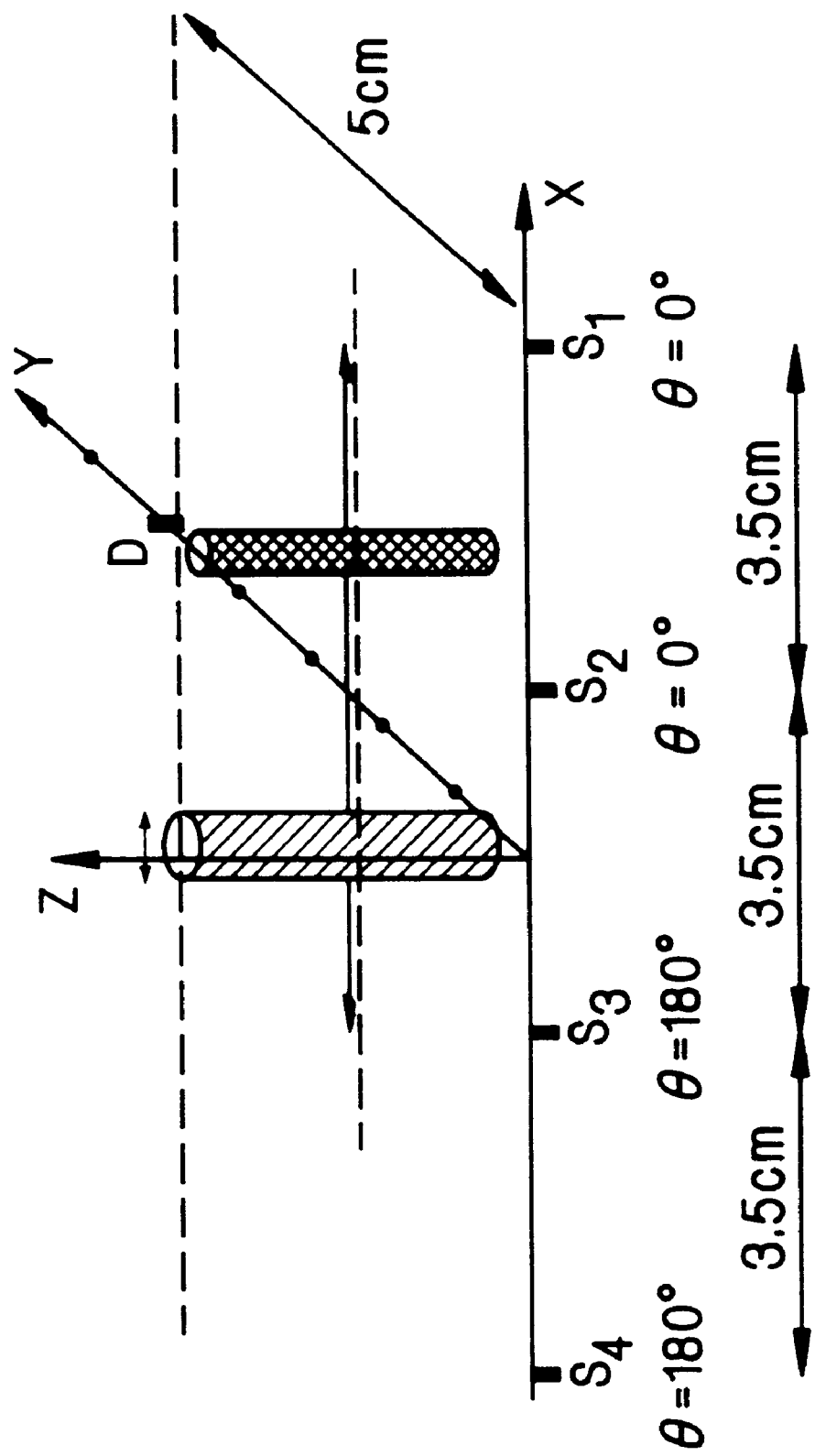
FIG. 10A displays an experimental arrangement of sources of a four element phased array, a detector, and two strongly absorbing objects.
Figure 10B:
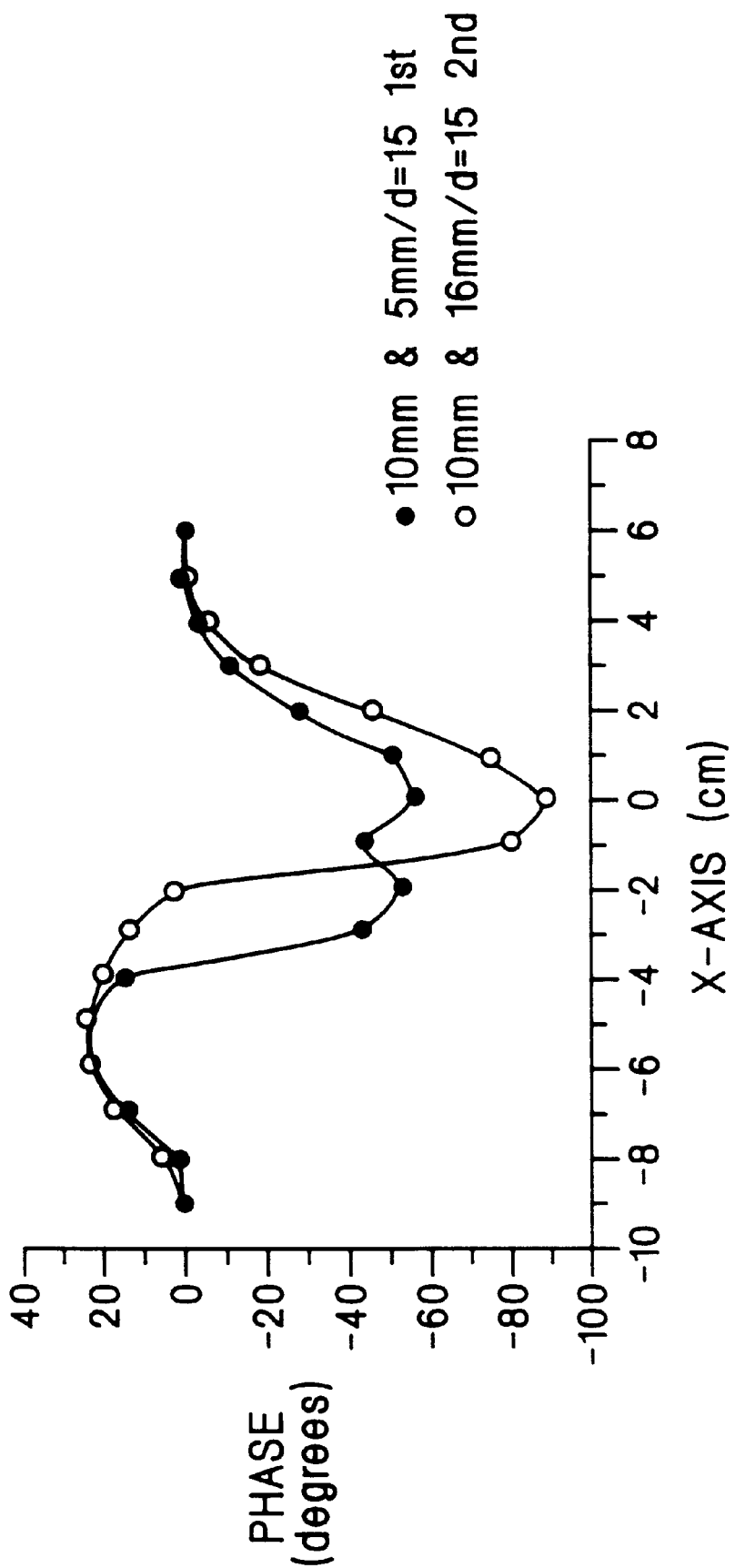
FIG. 10B displays the phase shifts measured for the four element array of FIG. 10A scanning two absorbing objects of different sizes.

Scanning of two objects of a different diameter is shown in FIG. 10A. Two cylinders of different diameter are scanned across the four element phased array located on the x-axis. The detection port in located at y=5 cm. In FIG. 10B the detected phase change in plotted against the displacement of these objects. Curve A represents the phase change of two cylinders of diameters 5 mm and 10 mm separated 3 cm apart. Curve B was measured using 16 mm cylinder instead the 5 mm cylinder. In this case, wherein the two cylinder separation is smaller, the phase detector can not resolve the two objects.

The imaging resolution is increased by increasing the number of elements of the phased array, since the main lobe of the resultant beam becomes much sharper, the gradient of photon density is larger. Phased arrays of different number of elements and different shapes are used for imaging different organs. For example, in tumor imaging, the four element phased array of FIG. 8A having an approximately linear shape can be used for imaging of the brain. On the other hand, a rectangular or a circular phased array would be used for imaging of a hidden tumor in the breast. The modulation frequency and the element spacing is adjusted to obtain proper focussing in each case.

Alternative embodiments of suitable optical imagers are disclosed in a PCT application PCT/US93/05868, filed Jun. 17, 1993, and published as International Publication No. WO 93/25145, which is incorporated by reference as if fully set forth herein.

In another embodiment, the present invention envisions imaging systems able to calculate the average migration pathlengths. Referring to FIGS. 1 and 1A, in one mode of operation, the signal from master oscillator 22 is mixed with a set of four local oscillators operating at offset frequencies of 25, 35, 45, and 55 kHz (not shown in FIGS. 1 and 1A); there is one local oscillator operating at an offset frequency associated with each laser diode. Thus, the output of each laser diode is intensity modulated at the master oscillator frequency plus the frequency of its local oscillator. The intensity modulated radiation of each laser diode is simultaneously coupled to the tissue.

Detection of the optical field is performed in the same way as described for the other embodiments. The detected signal is heterodyne mixed directly at the PMT detector. The detector outputs signals at four different offset frequencies associated with each diode. These signals are fed into the phase detector wherein the phase and the intensity of the detected radiation are measured. There are either four phase detectors (only one detector is shown in FIG. 1) operating alternatively at different frequencies or one phased detector is used in a time shared mode of operation. The phase shift and the intensity of a detected heterodyned signal depend on the tissue through which the scattered and absorbed radiation migrated. When using several radiation sources of selected carrier frequency and phase, the resulting radiation has directional properties and the detected intensity and phase shift depend on the pathlength along which the radiation was scattered and absorbed. The tissue properties are determined from the detected phase shift and intensity values and from the known input ports and detection port geometries. The measured average pathlengths, <L>, can also be determined. The detected phase shift is converted to an effective migration pathlength <L> by using the low frequency approximation $\theta=2\pi f<L>n/c$, wherein f is the modulation frequency, c is the speed of light (3×10$^8$ cm/s), and n is the refractive index of the medium. (For detailed discussion see Analytical Biochemistry, Vol. 195, pages 330–351, 1991 which is incorporated by reference as if fully set forth herein.)

Figure 5A:
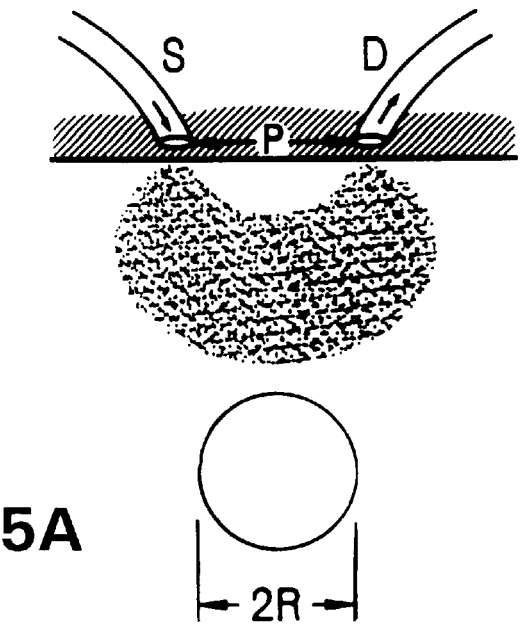
FIG. 5A, 5B, and 5C illustrate changes in optical field propagating in a strongly scattering medium which includes a strongly absorbing component.
Figure 5B:
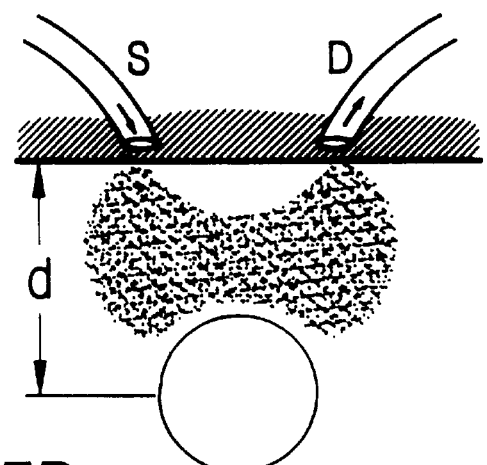
Figure 5C:
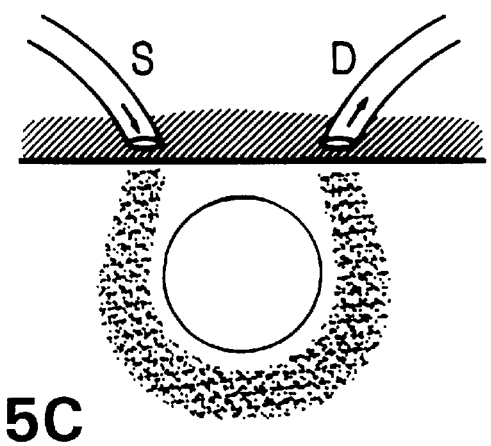

To illustrate imaging by detecting migration pathlengths, we use an example of photon migration in a tissue with a strongly absorbing object, a perfect absorber ($\mu_a\to\infty$) of radius R. Referring to FIGS. 5A, 5B, and 5C the distribution of pathlengths defines an optical field that exists between a point detector, D, and source, S, separated by distance ρ and located on the exterior of an examined tissue which is a semi-infinite, strongly scattering medium. As shown in FIG. 5A, infinitely far away from the field, a perfect absorber does not alter the banana-shaped optical field of photons emitted by source S and detected at detector D. As the object enters the optical field (FIG. 5B), the photons which have migrated the farthest distance from D and S are eliminated by the absorption process inside the perfect absorber of radius R. Since photons which travel the longest pathlengths are absorbed, the approach of an object shortens the distribution of pathlengths, or alternatively, shortens the average pathlength <L>. As the object moves closer, and the optical field surrounds the object (FIG. 5C), some of the detected photons have travelled "around" the object, which is detected as a lengthening the distribution of pathlengths. Thus, the average pathlength measurement can reveal location of a strongly absorbing component of a tissue (e.g., tumor or localized bleeding).

Even though this pathlength computation approach requires in most cases extensive computational capabilities, it can yield useful information in the localization procedures and can provide an useful supplement to the above described directional approach.

Figure 11:
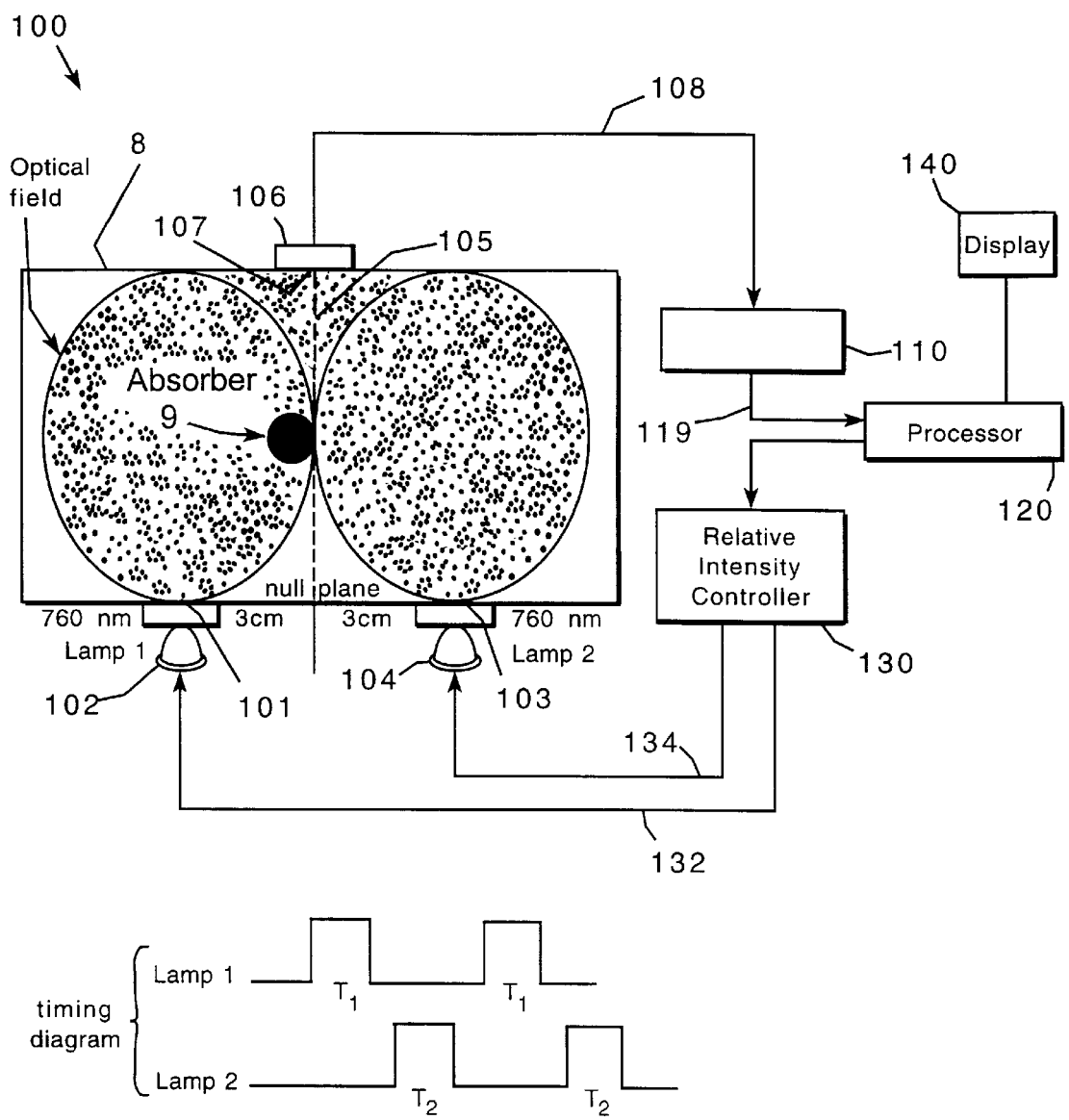
FIG. 11 shows diagrammatically a low frequency imaging system utilizing a one dimensional source array in accordance with the present invention.

In another preferred embodiment, shown in FIG. 11, a low frequency imaging system 100 includes two light sources 102 and 104 (e.g., tungsten lamps, LEDs) of electromagnetic radiation of a visible or infrared wavelength. The sources 102 and 104 introduce into examined tissue 8 at input locations 101 and 103, respectively, the radiation of known intensities that define a null plane 105 in tissue 8. A detection port, optically connected to a detector 106, is located at a detection location 107 of null plane 105. Detector 106 detects sequentially radiation that has migrated from the input locations 101 and 103 to detection location 107. A detector circuit 110, connected to detector 106, receives sequentially two detection signals 108, the first corresponding to radiation that has migrated from first input location 101 to detection location 107 and the second corresponding to radiation that has migrated from second location 103 to detection location 107. Detector circuit 110, includes a sample-and-hold circuit and a subtraction circuit constructed to subtract the first detection signal from the second detection signal. A processor 120 controls the entire operation, receives the differential signal 119 from detector circuit 110, governs the operation of intensity controller 130, and sends imaging data to a display 140.

Intensity controller 130 regulates the timing and the intensity on the radiation emitted from each source. For equal intensities of the emitted radiation, null plane 105 is located at a midpoint between the two optical field patterns generated from sources 102 and 104. Detector 106 is located at the null plane or at a known location relative to the null plane.

Referring to FIG. 11A, detector circuit 110 receives detection signal 108 from a diode detector 106. The circuit enables correction for the dark current/noise that comprises background light, DC offset of the operational amplifiers, photodiode dark current, temperature effects on the outputs of individual components and variations due to changing environment. The circuit also enables subtraction of the first detection signal from the second detection signal.

The system performs data acquisition in two cycles, each having four steps synchronized by its internal oscillator. In the first cycle, detecting light that has migrated from input location 101 to detection location 107, the first step is performed by having the light sources off. The output is directed to an integrator 112c and integration capacitor 113c is charged to the dark level voltage. In the second step, the first light source is turned on. The preamplifier output that corresponds to the intensity of the detected light is directed to integrator 112c in a way to charge capacitor 113c with current of polarity opposite to the polarity of the charging current in the first step. This is achieved using appropriate ON/OFF combination of switches A and B. The voltage of capacitor 113c is charging to a value which, at the end of this step, represents the total signal minus the dark level noise signal. In the third step, both switches A and B are turned OFF to disconnect both the positive unity gain and the negative unity gain operational amplifiers (112a and 112b). Then, the output of integrator 112c is moved via switch C to a hold circuit with integrator 112d which also functions as a low pass filter. The output is the first detection signal corrected for the background noise. In the fourth step, the switches A, B and C are open and switch D is closed in order to discharge capacitor 113c through a 47K resistor. At this point, the circuit of integrator 112c is reset to zero and ready for the first step of the second detection cycle.

The second detection cycle is again performed in four steps employing the second light source (L2) instead of the first light source (L1). After the second detection signal, corrected for the background noise, is obtained, the two detection signals are subtracted in module 110B and the deferential signal 119 is sent to processor 120.

Spectrophotometer 100 has two equivalent arrangements. The first arrangement shown in FIG. 11 includes two sources 102, 104 (or a single source optically coupled to two input ports) and single detector 106 with detection port 107 located an the null plane 105. The second arrangement includes a single source and two detectors. The source is optically coupled to an input port located on the null plane defined by the positions of the two detectors (or a single detector optically coupled to two detection ports). For substantially "homogeneous" tissue (i.e., normal tissue) or if a tumor is located symmetrically on the null plane, the detectors will detect a symmetric signal. Otherwise, the detectors will detect a asymmetric signal due to the modification of the optical field caused by the tumor having different scattering or absorption properties than the normal tissue.

Figure 14:
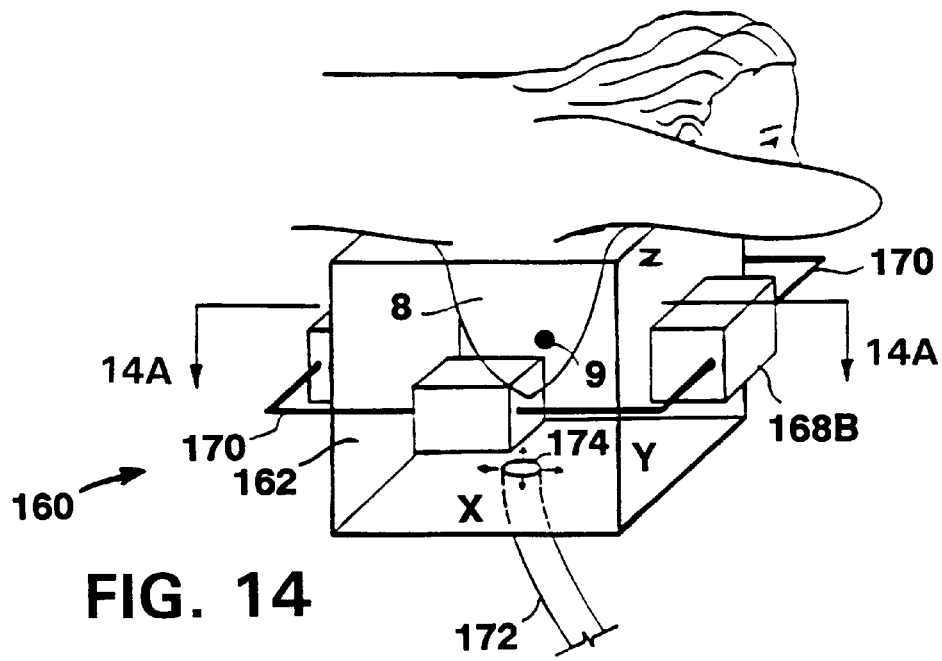
FIGS. 14 and 14A show a scanning system constructed for imaging of breast tissue.
Figure 14A:
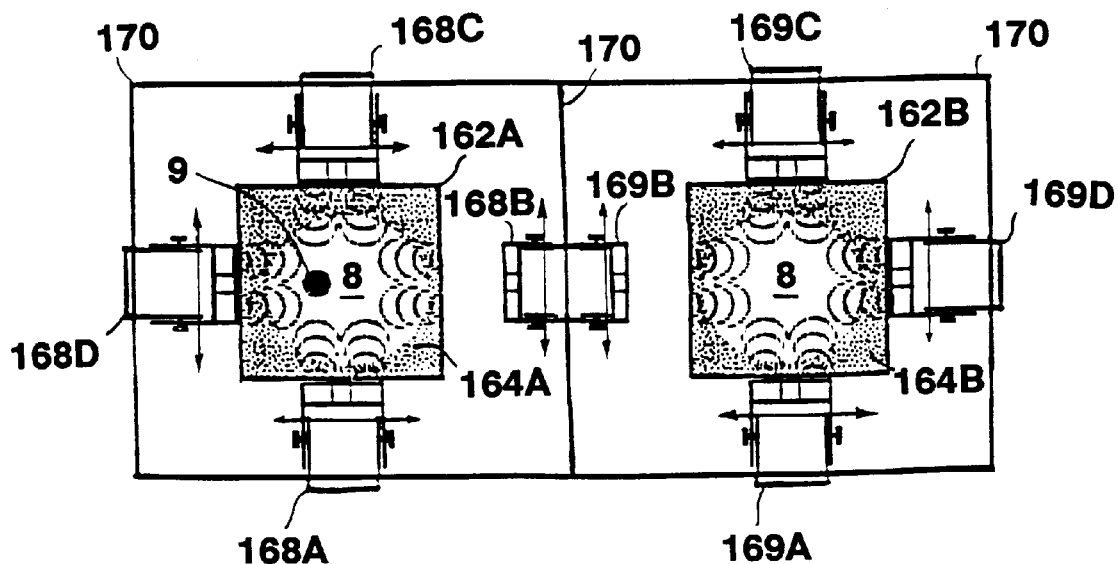

The source-detector geometry may be a transmission geometry as shown in FIG. 11 or a reflection geometry as shown in FIG. 14A. Another source-detector probe that utilizes a reflection geometry is disclosed in International Publication No. WO 92/20273, filed May 18, 1992, which is incorporated by reference as if fully set forth herein.

To examine a volume of tissue, the system may sweeps the null plane position over the examined tissue by changing the relative value of the intensities of the emitted radiation. Detector 106, which may include an array of detectors, is again located at the null plane or at a known location relative to the null plane. Alternatively, the null plane scanning is achieved by moving the input ports and the detection port to different locations, or by scanning the introduced light over the tissue surface by orienting a mirror.

Figure 12:
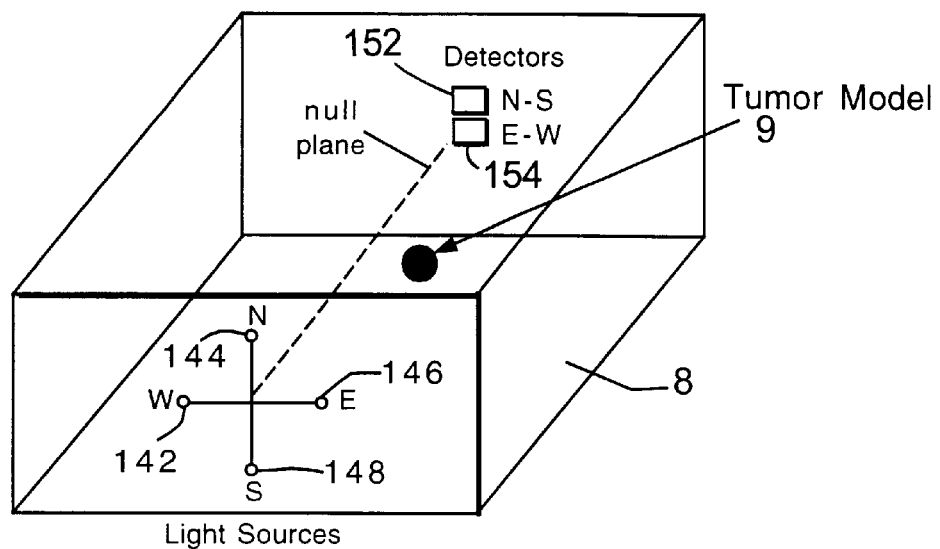
FIGS. 12 and 13 show diagrammatically a low frequency imaging systems utilizing a two dimensional source array in accordance with the present invention.
Figure 12:
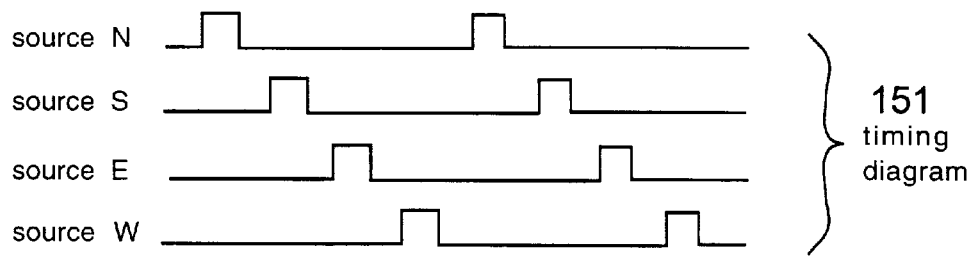
Figure 12:
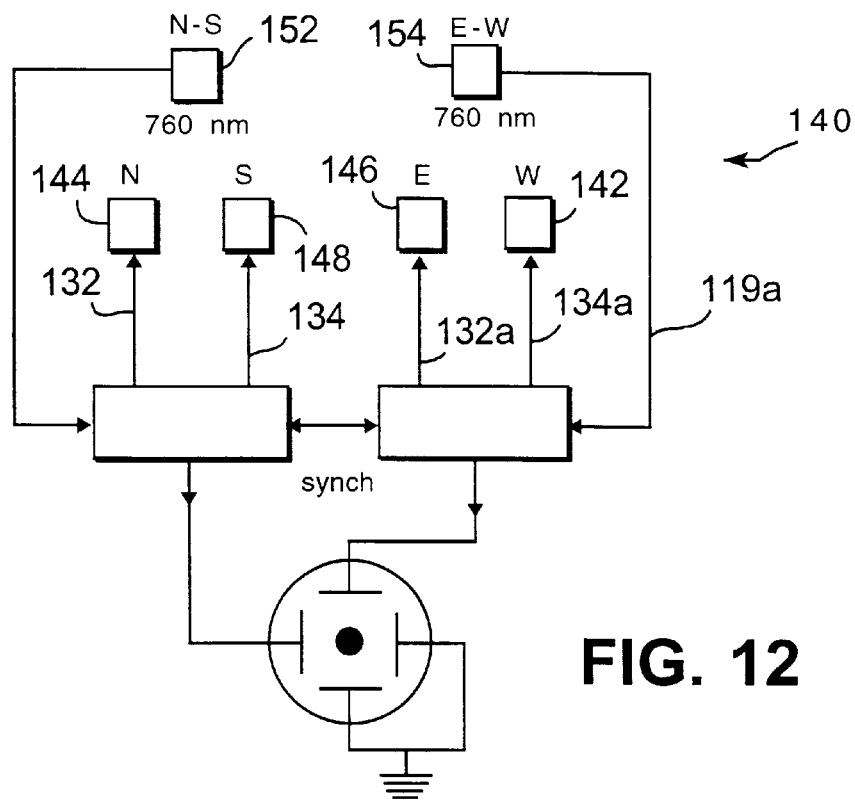
Figure 13:
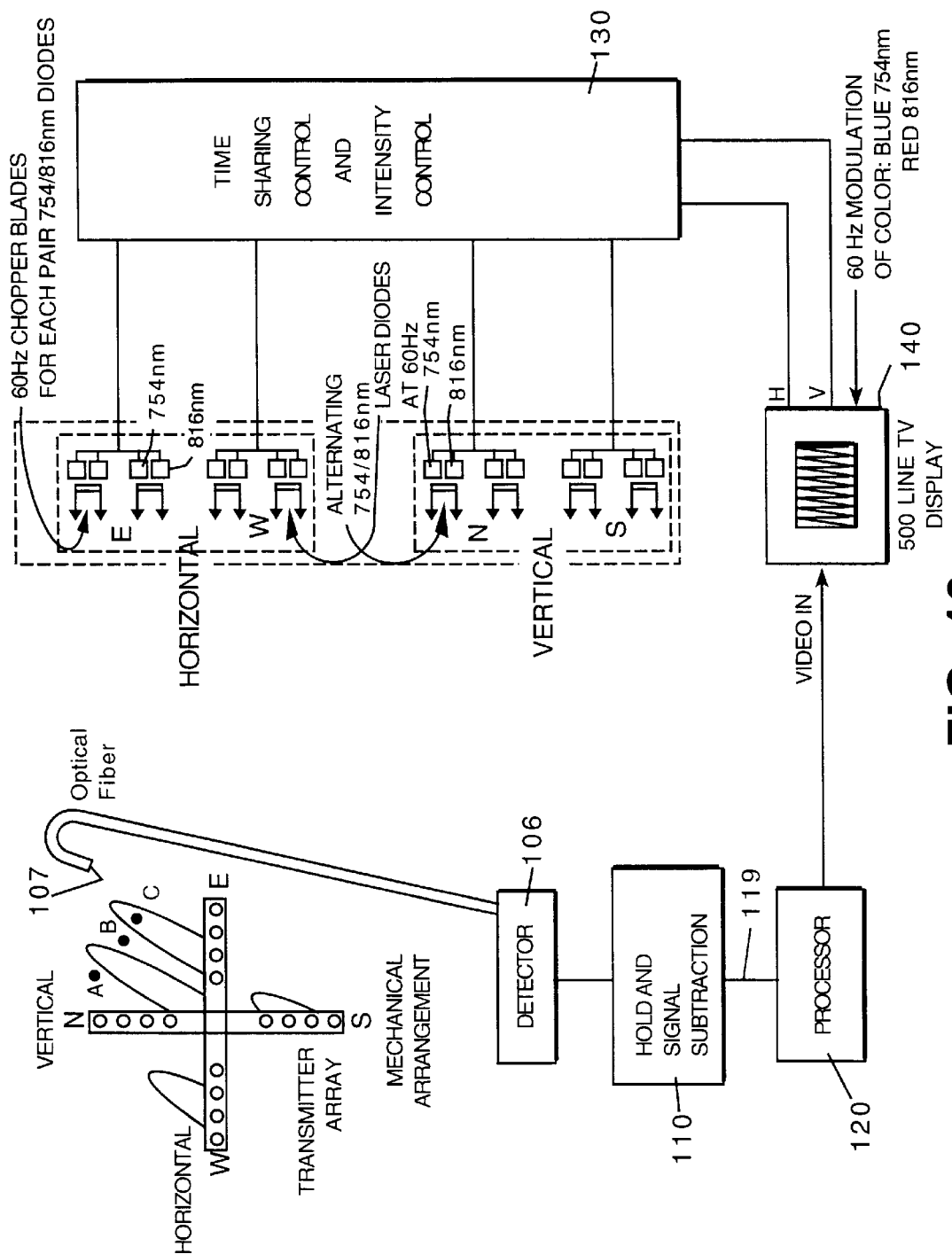

FIGS. 12 and 13 display another embodiment of the low frequency imaging system that utilizes a two dimensional array of light sources. Referring to FIG. 12, imaging system 140 includes four sources 142, 144, 146, and 148 (labeled W, N, E, and S) which are turned on and off as shown in a timing diagram 150. The system uses two differential detectors 152 and 154, located relative to the null plane, which produce deferential signals 119 and 199a, respectively, corresponding to the radiation emitted from sources 144, 148, and sources 142, 146. Referring to FIG. 13, imaging system 150 utilizes a two dimensional, dual wavelength array. The system operates based on similar principles as described for the imaging systems of FIGS. 11 and 12.

To increase resolution of the system an exogenous pigment sensitive to the introduced radiation (a light sensitive contrast agent) can be introduced, e.g., by injection, into the examined tissue. Then, the imaging system uses radiation of a wavelength sensitive to the exogenous pigment that also may be preferentially absorbed in a tumor located in the examined tissue. Alternatively, the imaging system uses radiation of a wavelength sensitive to an endogenous pigment of the examined tissue.

FIGS. 14 and 14A show a scanning system 160 constructed for imaging of breast tissue. Scanning system 160 may employ spectroscopic systems of FIGS. 1, 2 or 3, or systems of FIGS. 11, 12 or 13. Scanning system 160 includes an optical coupler 162, which may have cubical or cylindrical shape and is filled with optical medium 164. Optical coupler 162 is positioned over the breast near the chest wall. As described above in U.S. Pat. No. 5,402,778, which is incorporated by reference, the optical properties, pressure and volume of medium 164 may be controlled by an external system connected to the coupler by a set of tubes. The optical matching fluid (e.g., twice-diluted J&J baby lotion) is contained within pliable, optically an transparent barrier. The inside walls of coupler 162 may be coated with a film that reflects light in the visible or near infra-red range back to the matching fluid to prevent escape of photons from the tissue surface. The optical coupler may have different sizes or may have an adjustable volume so that the coupler can have a selected distance between the breast surface and the inside walls. (The preferred is distance is about 1 centimeter, but for a very small tissue a larger distance is preferable to achieve semi-infinite boundary conditions.) Thus the coupler is also useful for examination of the breast of a small size or after a surgical removal of the breast tissue. After placement of coupler 162, the volume of medium 164 is adjusted so that the barrier fits snugly around the examined breast. Alternatively, the optical medium is a pliable solid, for example, an absorbing gel containing metallic or oxide spherical particles, silky glass beads as scatterers or a suitable plastic material.

FIG. 14A depicts a set of couplers 162A and 162B for simultaneous scanning of both breasts. Attached to each coupler are source-detector probes (168A, 168B, 168C, 168D, 169A, 169B, 169C, 168D), which include one or more optical sources or detectors described above. The probes are movable on a rail 170. In an automatic positioning system, each probe is connected to a servo motor (step motor) that is operated by a controller. Depending on the spectroscopic system, a fiber 172 may be used to collect, at a detection port 174, radiation that has migrated in the examined tissue and couple the radiation to a detector. Alternatively, fiber 172 may be used to couple, at input port 174, radiation to the examined tissue.

In an electro-optic scan, a computer controller maintains coordinated positions of the probes to the selected combination of the transmitters and receivers. The scan is performed on a single breast or simultaneously on the contralateral breast. The sensitivity of the simultaneous scan is increased be measuring a differential signal. A computer displays the detected signal or the differential signal in a 3 dimensional coordinate system. To increase the resolution, a contrast agent (e.g., cardio-green, indocyanine-green) which is preferentially accumulated in a tumor may by injected intravenously. Several scans are performed to observe the time dependence of the decay and identify a location of a suspected anomaly. The system can also calculate the scattering coefficient and absorption coefficient of the suspected anomaly as in U.S. Pat. No. 5,402,778 and the reference cited therein.

The scan may be combined with a needle localization procedure, X-ray mammography or an MRI scan as is described in International Application WO 95/02987 (PCT/US94/07984, filed Jul. 15, 1994).

What is claimed is:

1. An optical system for in vivo, non-invasive examination of biological tissue, comprising:

at least one light source constructed to emit light of a visible or infra-red wavelength for introduction into an examined tissue volume from at least one input port;

at least one detector constructed to detect light of said wavelength that has migrated in the examined tissue volume from said at least one input port to at least one detection port;

an optical array of said input and detection ports located in a selected geometrical pattern providing several average photon migration pathlengths in the examined tissue volume, each arrangement of said at least one input port and said at least one detection port providing one of said average pathlengths that is characteristic of the tissue between said input and detection ports;

a radiation controller constructed to sequentially control light emitted from said at least one input port and constructed to control detection of said light of said wavelength to define a null plane in the tissue volume for two of said arrangements of said input and detection ports; and a processor, operatively connected to said radiation controller, constructed to examine the biological tissue based on data corresponding to said introduced and detected light for at least two of said average pathlengths and said defined location of said null plane.

2. The optical system of claim 1, wherein said radiation controller is constructed to control intensity of said light emitted sequentially from at least two input ports.

3. The optical system of claim 1, wherein said radiation controller is constructed to provide equal intensity of said light emitted sequentially from at least two input ports.

4. The optical system of claim 2, wherein said radiation controller is constructed to regulate said intensities in a manner that sweeps the null plane over the examined tissue volume.

5. The optical system of claim 1, wherein said radiation controller is constructed to control detection sensitivity of said light received at at least two detection ports.

6. The optical system of claim 5, wherein said radiation controller is constructed to regulate said detection sensitivity in a manner that sweeps the null plane over the examined tissue volume.

7. The optical system of claim 1, wherein said radiation controller is constructed to provide equal detection sensitivity of said light received at at least two detection ports.

8. The optical system of claim 1, wherein said input or detection ports are arranged as a linear array.

9. The optical system of claim 1, wherein said input or detection ports are arranged as a two dimensional array.

10. The optical system of claim 9, further including an image processor, connected to receive data from said processor, constructed to create image data for several of said average pathlengths and said defined locations of said null plane; and a display, connected to the image processor, constructed to display the image data representing the examined tissue.

11. The optical system of claim 10, wherein said wavelength is sensitive to an exogenous pigment of the examined tissue.

12. The optical system of claim 10, wherein said image processor is constructed to locate a tumor present in the examined tissue by employing said wavelength sensitive to an exogenous pigment.

13. The optical system of claim 1, wherein said optical array is arranged to examine breast tissue.

14. The optical system of claim 1, wherein said input or detection ports are arranged as a two dimensional array for examination of breast tissue and wherein said radiation controller is constructed to control said light emission and detection to provide two null planes intersecting in the examined tissue volume.

15. The optical system of claim 14, further including:
an image processor, connected to receive data from said processor, constructed to create image data for several of said average pathlengths and said defined locations of said null plane; and
a display, connected to the image processor, constructed to display the image data representing the examined breast tissue.

16. The optical system of claim 15, wherein said optical array is further arranged for co-operatively performing a needle localization procedure.

17. The optical system of claim 1, further including an oscillator and a phase detector, said oscillator being constructed to generate a carrier waveform of a frequency compatible with the phase shift that originates during photon migration over said average pathlength, said light source being coupled to said oscillator and constructed to generate said light modulated by said carrier waveform, said phase detector being constructed to measure the phase shift of a detected light waveform, of said detected light, relative to said modulated light waveform, said phase shift being indicative of scattering or absorptive properties of the examined tissue, and said processor being constructed to examine the tissue employing the phase shifts for said two average pathlengths defining said null plane.

18. The optical system of claim 17 wherein said oscillator operates at a frequency in the range of 40 MHZ to 1 GHz.

19. The optical system of claim 18, wherein said optical array is arranged to examine breast tissue.

20. The optical system of claim 19 further including:
an image processor, connected to receive data from said processor, constructed to create image data for several of said phase shifts representing several said average pathlengths; and
a display, connected to the image processor, constructed to display the image data representing the examined breast tissue.

21. The optical system of claim 17 wherein said radiation controller is constructed to provide equal intensity of said modulated light emitted sequentially from at least two input ports.

22. The optical system of claim 17 wherein said radiation controller is constructed to provide equal detection sensitivity for said modulated light received at at least two detection ports.

23. The optical system of claim 1, wherein said processor is further constructed to examine the biological tissue based on additional data corresponding to said introduced and detected light for at least two average pathlengths and said defined location of said null plane.

24. The optical system of claim 1, further comprising:
a second optical array of said input and detection ports located in a selected geometrical pattern providing several average photon migration pathlengths in a second examined tissue volume, said input port of said second array being optically connected to a second light source constructed to emit light of said wavelength for introduction into the second tissue volume, said detection port being optically connected to a second detector constructed to detect light of said wavelength that has migrated in the second tissue volume from said at least one input port of said second array to at least one detection port of said second array; and
a second radiation controller constructed to sequentially control light emitted from said input port of said second optical array and constructed to control detection, at said second detector, of said light of said wavelength to define a null plane in said second tissue volume for two of said arrangements of said input and detection ports of said second optical array;
wherein said processor is further connected to said second radiation controller and is constructed to receive data corresponding to said introduced and detected light for at least two of said average pathlengths in the second tissue volume and said defined location of said null plane, said processor being arranged to correlate data from said two tissue volumes.

25. The optical system of claim 24, wherein said first-mentioned and said second radiation controllers are arranged for simultaneous emission and detection of light at symmetrically located ports of said first-mentioned and said second optical arrays.

26. The optical system of claim 25 wherein said processor is further arranged to provide a differential signal for optical data obtained by said first-mentioned and said second optical arrays.

27. The optical system of claim 24, wherein said optical array is arranged to examine breast tissue.

28. An optical method for in vivo, non-invasive examination of biological tissue, comprising:
providing an optical array of input and detection ports located in a selected geometrical pattern providing several average photon migration pathlengths in an examined tissue volume, said input port being optically connected to a light source constructed to emit light of a visible or infra-red wavelength for introduction into the tissue volume, said detection port being optically connected to a detector constructed to detect light of said wavelength that has migrated in the examined tissue volume from said input port to said detection port; each arrangement of said input port and said detection port providing one said average pathlength that is characteristic of tissue between said input and detection ports;
emitting light from said input port and detecting light that has migrated in the examined tissue volume from said input port to said detection port;
controlling sequentially said light emission from said input port or said light detection to define a null plane in the tissue volume for two said arrangements of said input and detection ports;
correlating data corresponding to said introduced and detected light for at least two said average pathlengths with said defined location of said null plane; and
examining the biological tissue based on said correlation.

29. The optical method of claim 28, wherein said controlling includes controlling intensity of said light emitted sequentially from at least two said input ports.

30. The optical method of claim 29 wherein said intensity controlling includes regulating said intensities in a manner that sweeps the null plane over the examined tissue volume.

31. The optical method of claim 28 wherein said controlling includes providing equal intensity of said light emitted sequentially from at least two said input ports and said detecting includes detecting light at at least one said detection port located symmetrically with respect to said two input ports.

32. The optical method of claim 28 wherein said controlling includes controlling detection sensitivity of said light received at at least two said detection ports.

33. The optical method of claim 32, wherein said detection controlling includes regulating said detection sensitivity in a manner that sweeps the null plane over the examined tissue volume.

34. The optical method of claim 28, wherein said emitting includes emitting light from one input port, said controlling includes providing equal detection sensitivity of said light received at at least two detection ports, and said detecting includes detecting light received at said at least two detection ports with said equal sensitivity, said at least two detection ports being located symmetrically with respect to said one input port.

35. The optical method of claim 28, wherein said light emission and said light detection is performed using said input and detection ports arranged as a linear array.

36. The optical method of claim 28, wherein said light emission and said light detection is performed using said input and detection ports arranged as a two dimensional array.

37. The optical method of claim 36, further including
creating image data for several of said average pathlengths and said defined locations of said null plane; and
displaying the image data representing the examined tissue.

38. The optical method of claim 37, further includes introducing an exogenous pigment into the examined tissue volume and wherein said emitting said wavelength includes employing a wavelength sensitive to said exogenous pigment in the examined tissue.

39. The optical method of claim 38, further includes locating a tumor present in the examined tissue by employing said wavelength sensitive to said exogenous pigment.

40. The optical method of claim 28, wherein said light emission and said light detection is performed using said input and detection ports arranged to examine breast tissue.

41. The optical method of claim 28, wherein said light emission and said light detection is performed using said input and detection ports arranged as a two dimensional array for examination of breast tissue, and said controlling said light emission and detection provides two said null planes intersecting in the examined tissue volume.

42. The optical method of claim 41, further including:
creating image data for several of said average pathlengths and said defined locations of said null plane; and
displaying the image data representing the examined breast tissue.

43. The optical method of claim 42, wherein said light emission and said light detection is performed using said input and detection ports located in an optical coupler arranged for co-operatively performing the needle localization procedure.

44. The optical method of claim 28, further including
generating a carrier waveform of a frequency compatible with the phase shift that originates during photon migration over said average pathlength;
coupling said generated carrier waveform to said light source to generate light modulated by said carrier waveform;
measuring a phase shift of a detected light waveform, of said detected light, relative to said modulated light waveform, said phase shift being indicative of scattering or absorptive properties of the examined tissue; and
said correlating includes employing said phase shifts for said two average pathlengths defining said null plane.

45. The optical method of claim 44 wherein said generating said carrier waveform includes generating said frequency in the range of 40 MHZ to 1 GHz.

46. The optical method of claim 44 wherein said controlling includes providing equal intensity of said modulated light emitted sequentially from at least two input ports and said detecting includes detecting said modulated light at said at least one detection port located symmetrically with respect to said two input ports.

47. The optical method of claim 44 wherein said emitting includes emitting said modulated light from one input port, said controlling includes providing equal detection sensitivity for said modulated light received at at least two detection ports, and said detecting includes detecting light received at said at least two detection ports with said equal sensitivity, said at least two detection ports being located symmetrically with respect to said one input port.

48. The optical method of claim 44, wherein said light emission and said light detection is performed using said input and detection ports arranged to examine breast tissue.

49. The optical method of claim 48, further including:
creating image data for several of said average pathlengths and said defined locations of said null plane; and
displaying the image data representing the examined breast tissue.

50. The optical method of claim 28 wherein said correlation and examination is further performed based on additional data corresponding to said introduced and detected light for at least two said average pathlengths and said defined location of said null plane.

51. The optical method of claim 28 further comprising:
providing a second optical array of input and detection ports located in a selected geometrical pattern providing several average photon migration pathlengths in a second examined tissue volume, said input port of said second array being optically connected to a second light source constructed to emit light of said wavelength for introduction into the second tissue volume, said detection port being optically connected to a second detector constructed to detect light of said wavelength that has migrated in the second tissue volume from said input port to said detection port;
emitting light from said input port of said second array and detecting light that has migrated in the second tissue volume from said input port to said detection port of said second array; and
controlling sequentially said light emission from said input port of said second array or said light detection to define a null plane in the second tissue volume for two of said arrangements of said input and detection ports of said second array;
wherein said correlating includes correlating data corresponding to said introduced and detected light in the second tissue volume for at least two said average pathlengths with said defined location of said null plane in said second tissue volume; and wherein said examining includes examining the biological tissue based on said correlation of said data from said two tissue volumes.

52. The optical method of claim 51 wherein said controlling includes simultaneous emission and detection of light at symmetrically located ports of said first-mentioned optical array and said second optical array.

53. The optical method of claim 51 wherein said emitting light from said input port includes introducing light into breast tissue and said detecting includes detecting light that has migrated in the breast tissue for both the left breast and the right breast.

54. The optical method of claim 53, wherein said correlating further includes providing a differential signal for optical data obtained by said first-mentioned and said second optical arrays.

* * * * *